United States Patent
Van Der Westhuizen et al.

(10) Patent No.: US 9,296,717 B2
(45) Date of Patent: Mar. 29, 2016

(54) SYNTHESIS OF C-3 COUPLED BIFLAVONOIDS AND C-3 COUPLED BIFLAVONOID ANALOGUES

(75) Inventors: Jan Hendrik Van Der Westhuizen, Bloemfontein (ZA); Susanna Lucia Bonnet, Bloemfontein (ZA); Mathew Achilonu, Bloemfontein (ZA); Miroslav Sisa, Bloemfontein (ZA)

(73) Assignee: UNIVERSITY OF THE FREE STATE, Bloemfontein (ZA)

( * ) Notice: Subject to any disclaimer, the term of this patent is extended or adjusted under 35 U.S.C. 154(b) by 0 days.

(21) Appl. No.: 13/391,129

(22) PCT Filed: Aug. 19, 2010

(86) PCT No.: PCT/IB2010/053755
§ 371 (c)(1),
(2), (4) Date: Jul. 10, 2012

(87) PCT Pub. No.: WO2011/021167
PCT Pub. Date: Feb. 24, 2011

(65) Prior Publication Data
US 2012/0289715 A1   Nov. 15, 2012

(30) Foreign Application Priority Data
Aug. 19, 2009   (ZA) .................................. 2009/05765

(51) Int. Cl.
*C07D 311/28*   (2006.01)
*C07D 311/26*   (2006.01)
*C07D 407/10*   (2006.01)

(52) U.S. Cl.
CPC .................................... *C07D 311/28* (2013.01)

(58) Field of Classification Search
CPC ... C07D 311/28; C07D 311/26; C07D 407/10
USPC .................................................. 549/403, 399
See application file for complete search history.

(56) References Cited

PUBLICATIONS

Liu, F.,"SAR by Oxime-Containing Peptide Libraries: Application to Tsg101 Ligand Optimization." Chembiochem 9.12 (2008): 2000-2004.*
Patonay, T. et al. "Flavonoids. 43 [1,2]. Deprotonation-initiated Aryl Migration with Sulfur Dioxide Extrusion: A Route to 2,3-Dihydro-2,3-diaryl-3-hydroxy-4*H*-1-benzopyran-4-ones" *Journal of Heterocyclic Chemistry*, 1993, 30:145-151.
Li, Y.L. et al. "Study on the Synthesis of Some New Biflavonoids. VIII: A New Synthesis of $C_3$-Linked Biflavones, Bithioflavones and Bithiochromones" *Synthetic Communications*, 1993, 23(8):1075-1080.
Rahman, M. et al. "Synthesis of Biologically Relevant Biflavanoids—A Review" *Chemistry & Biodiversity*, 2007, 4:2495-2527.
International Search Report in International Application No. PCT/IB2010/053755, filed Aug. 19, 2010.

* cited by examiner

*Primary Examiner* — Samantha Shterengarts
*Assistant Examiner* — Matt Mauro
(74) *Attorney, Agent, or Firm* — Saliwanchik, Lloyd & Eisenschenk

(57) ABSTRACT

The preparation of C-3 coupled biflavonoids and C-3 coupled biflavonoid analogs occurs from flavan-3-ones that are contacted with a compound having a nucleophilic aromatic moiety, in the presence of a Lewis acid where an intermediate compound is formed with a C-3 hydroxy group. A flavan-3-ol can be converted to a flavan-3-one as required. The intermediate compound is dehydrated to a flavene with a C-3-C-4 double bond. The flavene compound undergoes hydroboration-oxidation hydration to introduce a C-4 hydroxy group that can be oxidized to an oxo group or can be dihydroxylation to introduce hydroxy groups at the C-4 and C-3 carbons and dehydrated to a biflavonoid or biflavonoid analog having an oxo group at its C-4 carbon and substituted by the selected nucleophilic aromatic moiety on its C-3 carbon.

8 Claims, No Drawings

SYNTHESIS OF C-3 COUPLED BIFLAVONOIDS AND C-3 COUPLED BIFLAVONOID ANALOGUES

CROSS-REFERENCE TO RELATED APPLICATIONS

This application is the U.S. national stage application of International Patent Application No. PCT/IB2010/053755, filed Aug. 19, 2010, which claims priority to South African Application No. 2009/05765, filed Aug. 19, 2009, the disclosures of each of which are incorporated herein by reference in their entirety.

FIELD OF THE INVENTION

The present invention relates to a novel process for the preparation of C-3 coupled biflavonoids and C-3 coupled biflavonoid analogues.

BACKGROUND TO THE INVENTION

Bi- and triflavonoids represent a diverse family of dimers, trimers, and oligomers of flavonoid monomers that are not linked via the C-4 heterocyclic carbon and are consequently not classified as proanthocyanidins. They, unlike the proanthocyanidins, do not form coloured anthocyanidins upon treatment with acids. The flavonoids characteristically have a carbonyl group or equivalent at the C-4 position (Figure 1). Together with proanthocyanidins, the bi- and triflavonoids constitute the two major classes of "complex $C_6$-$C_3$-$C_6$ secondary metabolites" (Ferreira; D; Slade, D; Marais, J. P. J. *Flavonoids Chemistry, Biochemistry and Applications*, edited by Øyvind M. Andersen Kenneth R. Markhams, CRC press 2006, 553-615, 1102-1135).

Figure 1: The structures of some bi- and triflavonoids

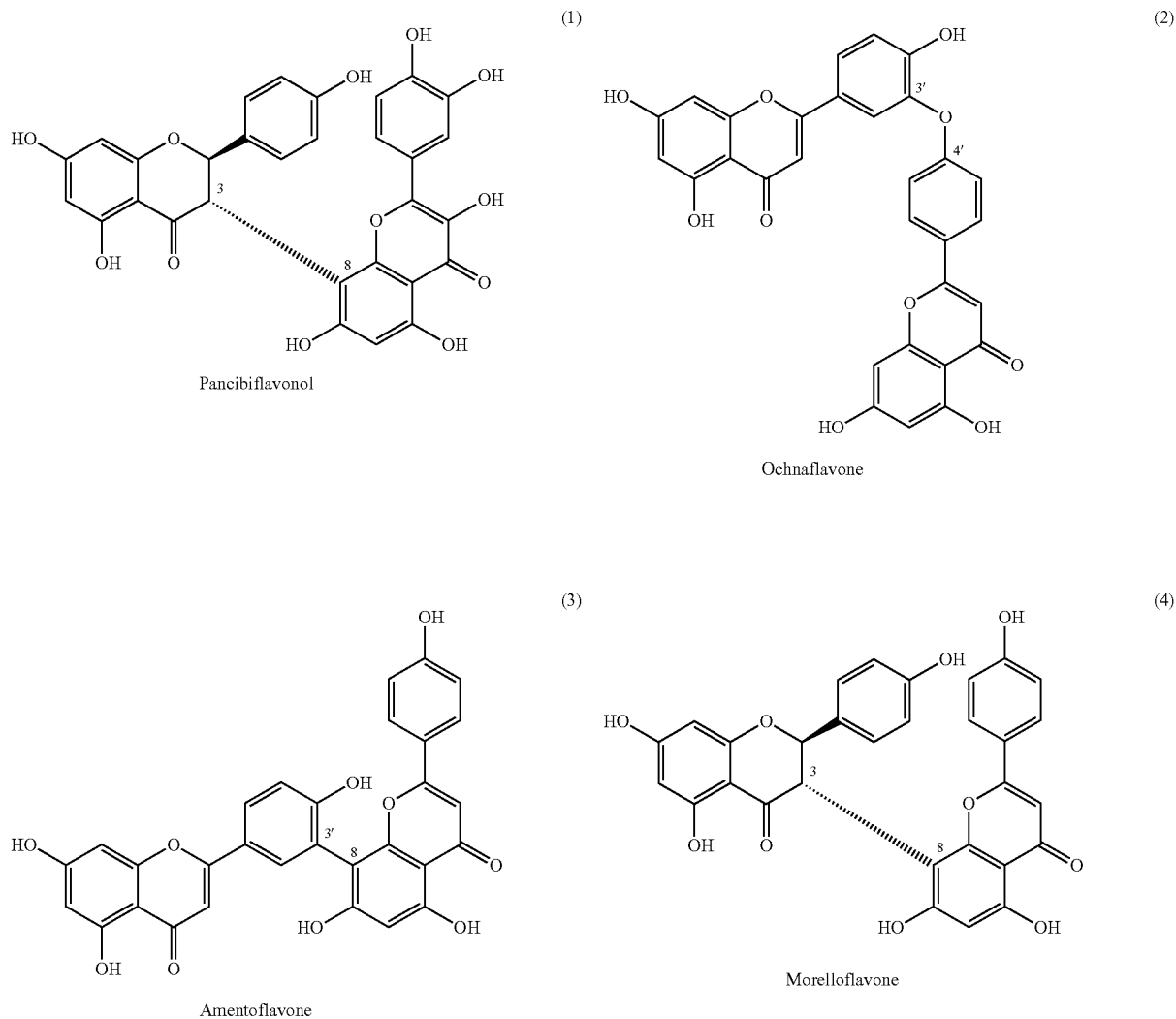

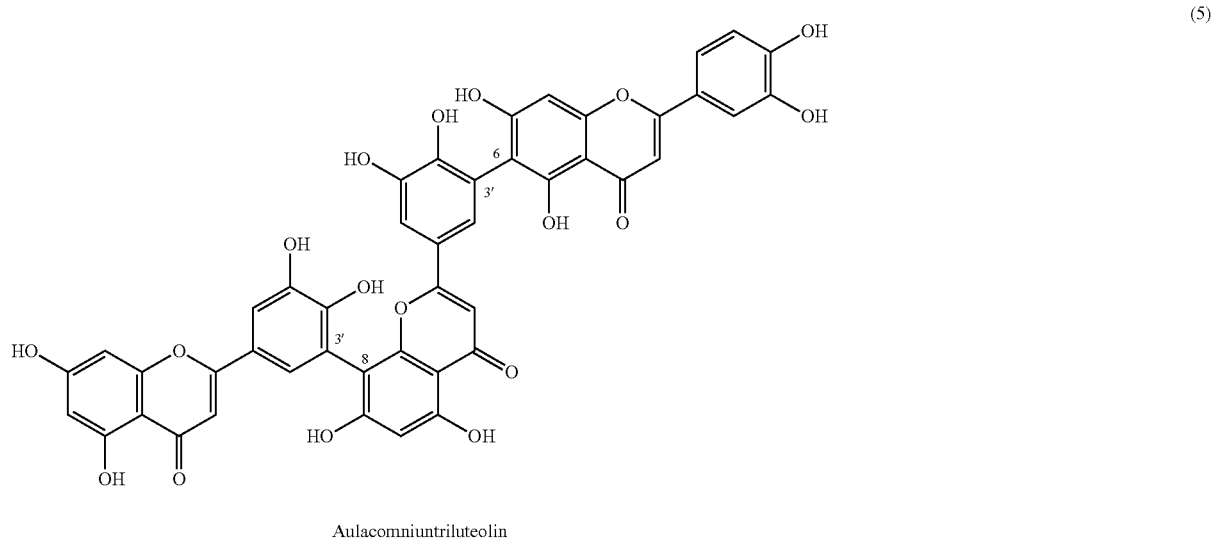

Aulacomniuntriluteolin

Bi- and triflavonoids that occur in nature are thought to be the products of phenol oxidative coupling of chalcones, aurones, auronols, isoflavones, flavanones, dihydroflavanols, flavanols and flavones. This contrasts with natural proanthocyanidins that are thought to be products of nucleophilic substitution of an hydroxy leaving group at C-4 of flavan-3,4-diols (via a C-4 carbocationic intermediate or via an $S_N2$ reaction). The oxidative nature of carbon-carbon bond formation leads to preservation of the substituents at C-4 of the starting materials. Tetra-, penta-, and hexaflavonoids have also been isolated and identified, and these compounds are also included in the class of bi- and triflavonoids. The Locksley system of nomenclature for bi- and triflavonoids has been applied in the present specification. (Locksley, H. D. Fortschr. Chem. Org. Naturst. 1973, 30, 207 and Rahman, M.; Riaz, M.; Desai, U. R. Chem. & Biodiv. 2007, 4, 2495-2527; and refs therein) However, Locksley's suggestion that biflavonoids be referred to as biflavanoids has not been followed herein.

Compounds with a carbonyl group at C-4 that do not arise from phenol oxidative coupling of monomeric flavonoids, including compounds linked via carbon-oxygen bonds, have been reported as bi- or triflavonoids.

A growing number of "mixed" dimers e.g. flavan-3-ol→flavonol {e.g. fisetinidol-[4α→2']-myricetin (6)}, originating from oxidative coupling of flavan-3-ols to flavonoids, has been isolated and belongs to both classes.

Figure 2: Fisetinidol-[I-4a][II-2']-myricetin

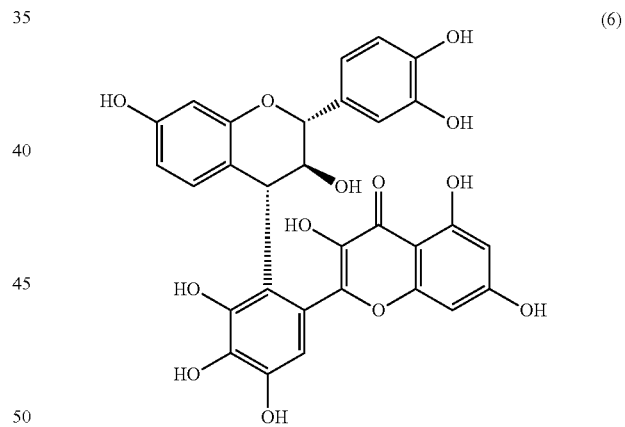

The structural diversity of bi- and triflavonoids makes the development of general synthetic methods impossible.

For simplicity, bi- and triflavonoids have, in terms of this specification, been categorised into four classes, depending on the nature and position of the interflavonoid bond:

Class 1: Bi- and triflavonoids where the carbon-carbon link is between aromatic rings. A plethora of synthetic methods exists to construct carbon-carbon inter-aromatic bonds (including Suzuki and Stille coupling reactions). These can be applied directly to bi- and triflavonoid synthesis (Miyaura, N.; Suzuki, A. Chem. Rev. 1995, 95, 2457; Muller, D.; Fleury, J.-P. Tetrahedron lett. 1991, 32 (20), 2229-2232; and Stille, J. K. Angew. Chem., Intl. Ed. Engl. 1986, 25, 508).

Class 2: Bi- and triflavonoids where the carbon-carbon link between the aromatic rings are replaced with a carbon-oxygen-carbon bond. Many synthetic methods exist to construct these inter-aromatic bonds (including the Ullmann coupling). These can be applied directly to bi- and triflavonoid synthesis (Nakazawa, K.; Ito, M. *Chem. Pharm. Bull.* 1963, 283; Ahmed, S.; Razaq, S. *Tetrahedron* 1976, 32, 503; and Zhang, F.-J.; Lin, G.-Q.; Huang, Q.-C. *J. Org. Chem.* 1995, 60, 6427).

Class 3: Bi- and triflavonoids where the carbon-carbon link is between the aromatic ring of one constituent monomer and the heterocyclic C-ring of another constituent monomer. As coupling of an aromatic ring on the 4-position of one constituent monomer will result in a proanthocyanidin, it leaves only C-2 and C-3 to couple. (I-3 and I-2 biflavones, including GB-flavones [I-3, II-8]-coupling and I-2 and I-3 bi-isoflavones). No I-2 biflavones have ever been isolated, unless one considers A-type proanthocyanidins as biflavonoids. Despite the interest that these I-3 flavones had received and their considerable pharmaceutical potential, no methods exists to synthesize any examples from this class (Ding, Y.; Li, X.-C.; Ferreira, D. *J. Org. Chem.* 2007, 72 (24), 9010-9017; Rucksthl, M.; Beretz, A.; Anton, R.; Landry, Y. *Biochem. Pharmacol.* 1979, 28, 535; Iwu, M. M.; Igboko, O. A.; Okunji, C. O.; Tempesta, M. S. *J. Pharm. Pharmacol.* 1990, 42, 290; Amelia, M.; Bronne, C.; Briancon, F.; Hagg, M.; Anton, R.; Landry, Y. *Planta Med.* 1985, 51, 16; Sun, C.-M.; Syu, W.-J.; Huang, Y.-T.; Chen, C.-C.; Ou, J.-C. *J. Nat. Prod.* 1997, 60, 382; Lin, Y.-M.; Flavin, M. T.; Cassidy, C. S.; Mar, A.; Chen, F. C. *Bioorg. Med. Chem. Lett.,* 2001, 11, 2101; Chang, H. W.; Baek, S. H.; Chung, K. W.; Son, K. H.; Kim, H. P.; Kang, S. S. *Biochem. Biophys. Res. Commun.* 1994, 205, 843).

Class 4: Bi- and triflavonoids where the carbon-carbon link is between the heterocyclic C-rings.

Bi- and triflavonoids formed in accordance with class 3 have been proven to have biological activity in a variety of screens. Progress in drug development is, however, hampered because no stereoselective synthetic access exists to obtain larger quantities of pure compounds and all research is based on molecules isolated in small quantities from natural sources.

Optically active compounds are highly desirable and are characterized in that the compounds include at least one asymmetric carbon and that the resultant stereoisomers or enantiomers are not present in 50:50 racemic mixture but display an enantiomeric abundance or excess of one of the enantiomers. Such excess or abundance results in the property of the compound to cause rotation of the orientation of polarized light passed through a solution thereof, hence for its so-called optical activity. In the most preferred form an optically active compound would have only one enantiomer present in a composition thereof, and such compositions are thus referred to as being enantimerically pure. The Applicant is not aware of any literature describing synthetic methods to obtain examples of class 3 bi- and triflavonoids in enantiomerically pure or optically active forms or from flavan-3-ols, despite the fact that morelloflavone (4) exhibits anti-inflammatory activity. This invention is accordingly in particular concerned with the preparation of optically active biflavanoid compounds and biflavanoid analogue compounds but is also applicable to the preparation of optically inactive compounds which are produced from optically inactive starting materials as will be described in more detail below.

Ferreira and co-workers speculated about the intermediacy of a quinomethane radical (38) or (39) in the biosynthesis of naturally occurring 2,7-bibenzofuranoids (40) from maesopsin (41) or an α-hydroxychalcone (42) (Scheme 1) [Bekker, R.; Ferreira, D.; Swart, K. J.; Brandt, E. V. *Tetrahedron* 2000, 56, 5297-5302].

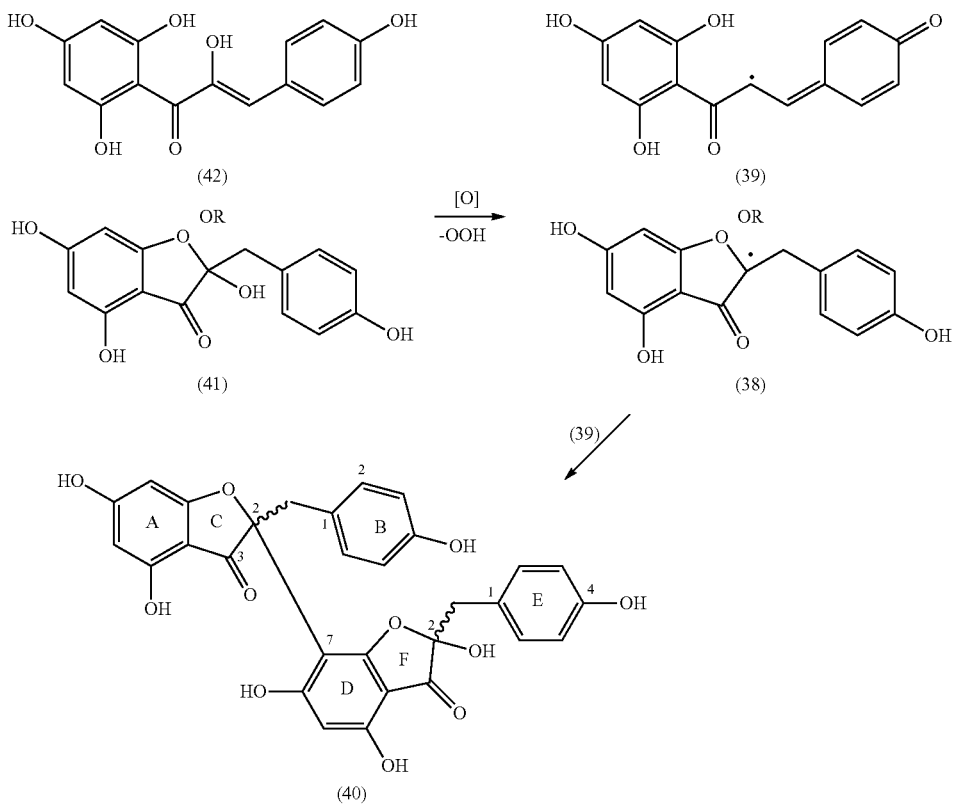

Scheme 1: Proposed biosynthesis of bibenzofuranoids

It has been submitted that the synthesis of the first natural [I-4, II-3″] bi-isoflavonoid (43), isolated from *Dalbergia nitidula* and synthesized by Roux and co-workers (Brandt, E. V.; Bezuidenhoudt, B. C. B.; Roux, D. G. *J. Chem. Soc., Chem. Commun.* 1982, 1408-1410 and Bezuidenhoudt, B. C. B.; Brandt, E. V.; Roux, D. G. *J. Chem. Soc., Perkin Trans. I* 1984, 2767-2778) via nucleophilic attack on an isoflavanyl-4-carbocation, generated from a pterocarpan (44), is a special case of the C-4 arylsubstituted proanthocyanidin syntheses. The B-ring of the isoflavanyl nucleophile is more oxygenated and reactive than its A-ring and a C4→C3′-linkage is formed (Scheme 2).

Scheme 2: Synthesis of a bi-isoflavonoid via nucleophilic substitution at C-4

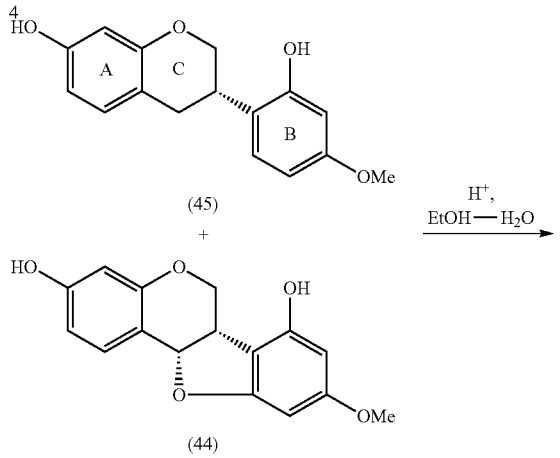

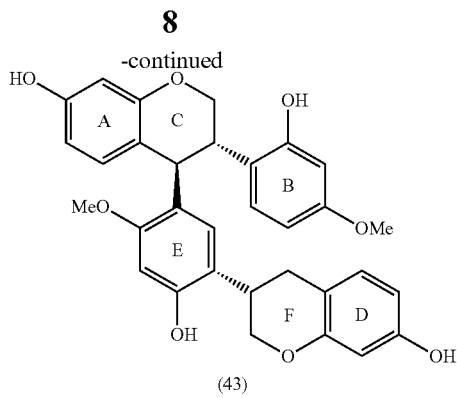

(43)

Donnelly and co-workers (Donnelly, D. M. X.; Fitzpatrick, B. M.; Ryan, S. M.; Finet, J.-P. *J. Chem. Soc., Perkin Trans. I* 1994, 1794-1801) synthesized the biflavonoids (46) and (47) via arylation of a 3-phenylsulfanylflavanone (48) with an 8-triacetoxyplumbylflavan derivative (49) (2:1 mixture of cis and trans). The dioxolane ring, of the intermediate (50) was cleaved during acid workup. Desulfurization of the intermediate (50) with nickel boride ($NaBH_4/H_2O$, $NiCl_2 6H_2O$/EtOH) yielded a chalcone (51) (in a 1.1:1 ratio of E/Z) that was cyclised with anhydrous sodium acetate in refluxing ethanol to the 3,8-biflavanone (46) in 73% yield (only the 2,3-trans isomer was isolated from a mixture of diastereoisomers with an α/β ratio of 1.4:1). Oxidation of (46) with dimethyldioxirane in acetone yielded (47) in 47% yield (Scheme 3). The end products are however not optically active and constitute a racemic mixture.

Scheme 3: Aryllead triacetate-mediated synthesis of biflavonoids

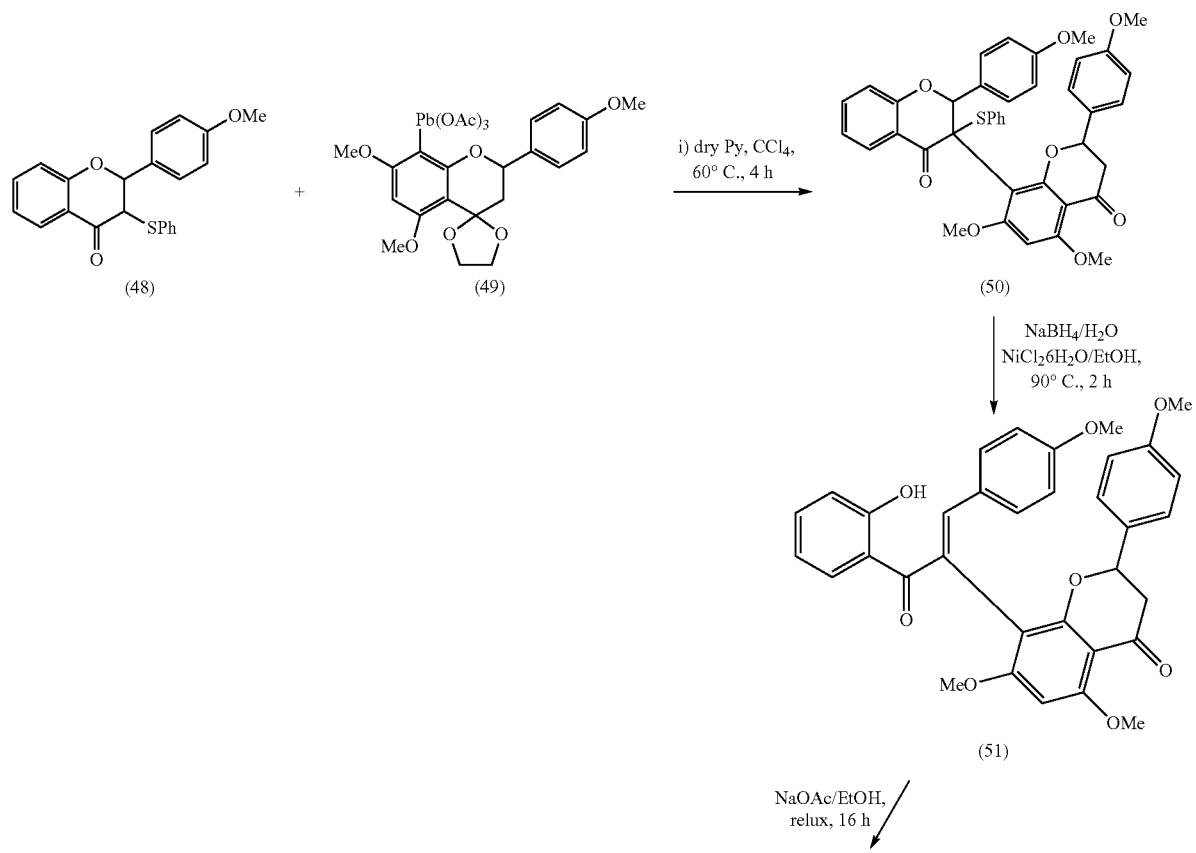

-continued

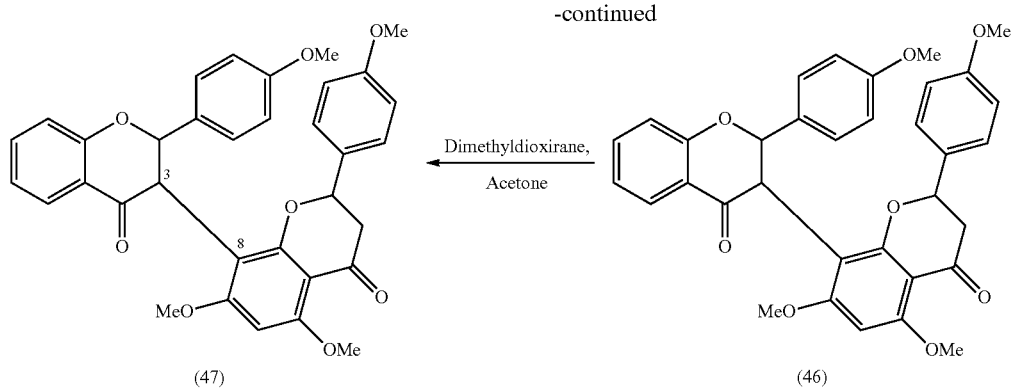

Synthesis of the isoflavone-isoflavone dimer (52), isolated from *Dalbergia nitidula* posed a challenge. It is linked via an electron deficient β-carbon in an α,β-unsaturated carbonyl moiety and no simple biomimetic equivalent of the proanthocyanidin syntheses was available. Ferreira and co-workers tried a variety of options, including coupling of nucleophilic phenolic units to aromatic oxygenated isoflavone-2,3-epoxides, direct coupling of phenolic units to isoflavones in a 1,4-Michael fashion, linkage of phenolic units to the acetal-type electrophilic centre of the intermediate in isoflavone synthesis prior to heterocycle construction (thallium(III)nitrate strategy) (Farkas, L.; Gottsegen, A.; Nogradi, M.; Antus, S. *J. Chem. Soc., Perkin Trans. 1* 1974, 305 and Antus, S.; Farkas, L.; Gottsegen, A.; Kardos-Balogh, Z.; Nogradi, M. *Chem. Ber.* 1976) and condensation of a $C_{16}$ (5'-formylated isoflavan) (53) with a $C_{14}$-unit (2-hydroxydeoxybenzoin) (54) in a modified Baker-Venkataraman reaction (Wagner, H.; Farkas, L. In: '*The Flavonoids*', ed. J. B. Harbome, T. J. Mabry, and H. Mabry, Chapman and Hall, London, 1975, 138). The last strategy succeeded in producing the target dimer (52) (Scheme 4). The biflavanoid moiety of these end products are also not optically active.

Scheme 4: Synthesis of a C-ring dimer via a modified Baker-Venkataraman process

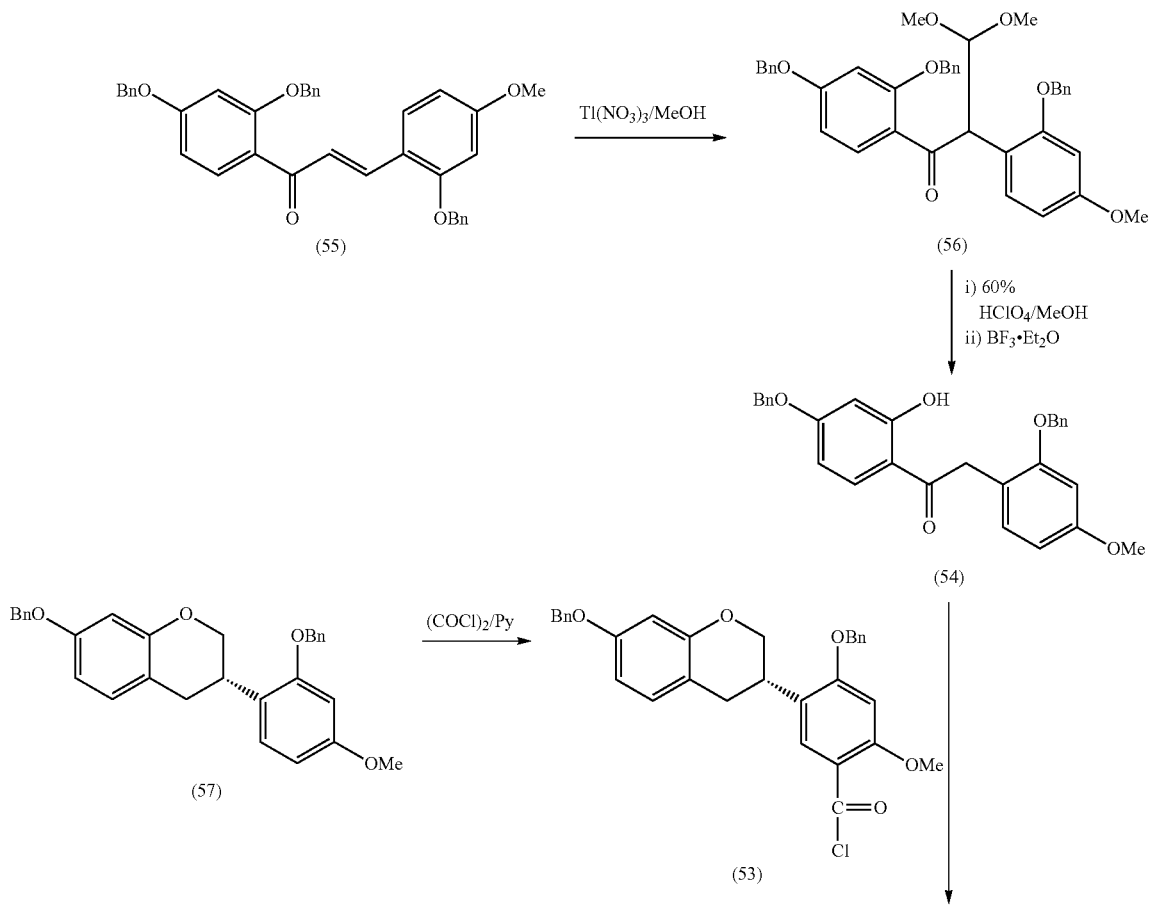

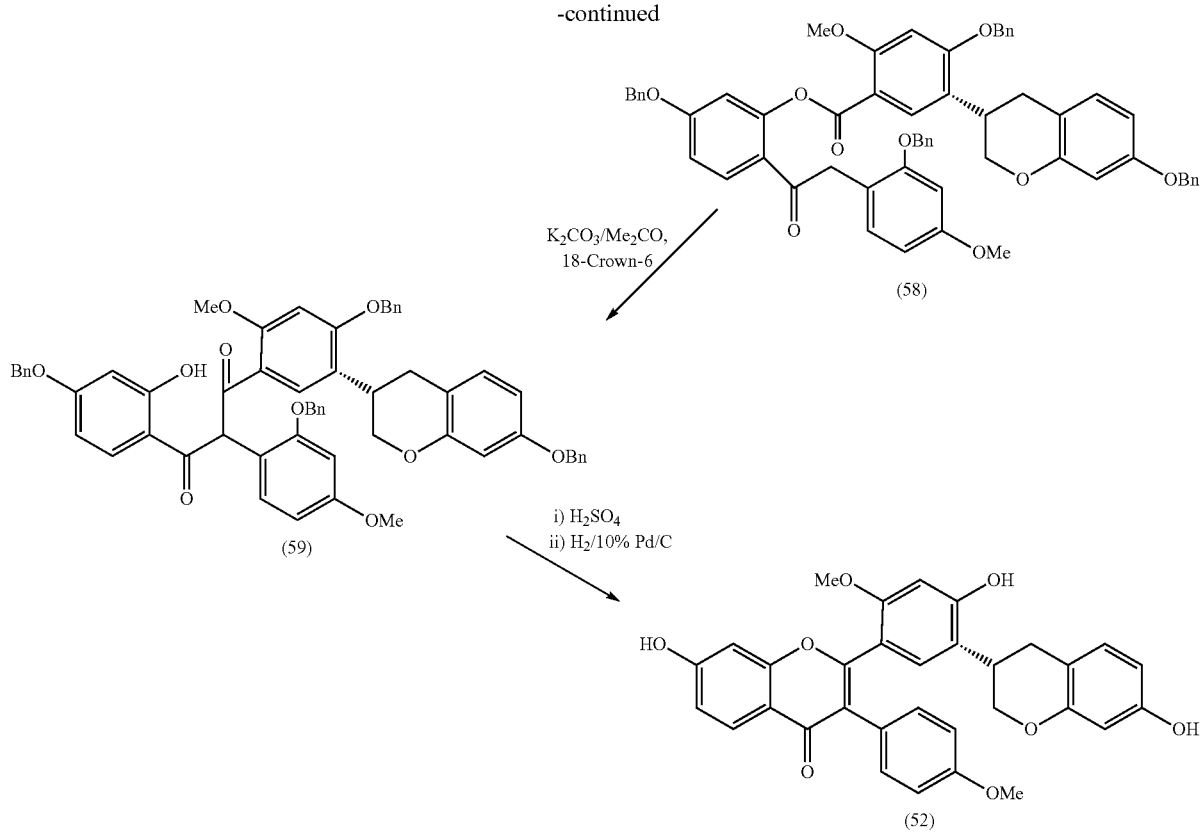

The carboxylic moiety in (53) (the $C_{16}$ unit) was introduced via formylation of the B-ring of (57) with the photochemical Reimer-Tieman reaction (Hirao, K.; Yonnemitsu, O. J. Chem. Soc., Chem. Commun. 1972, 812 and Hirao, K.; Ikegame, M.; Yonnemitsu, O. Tetrahedron 1974, 30, 2301). The deoxybenzoin (54) (the $C_{14}$ unit) was obtained from oxidation of the chalcone (55) with $Tl(NO_3)_3$ to (56) followed by decarbonylation with perchloric acid.

In light of the above, it is evident that methods which achieve replacing the 3-hydroxy group of flavan-3-ols with a carbon-carbon bond and retains the optical activity of the starting material remain an elusive goal. This would open the way to a plethora of new classes of flavonoids, including naturally occurring 3-coupled biflavonoids (I-3, II-6/8 biflavonoids).

In this specification the expression "flavonoid compounds" is used to denote compounds which are based on the flavonoid base structure represented by the general formula F Formula F

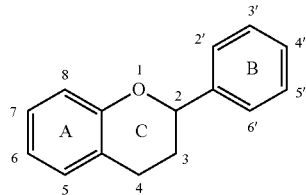

and in which carbons C-2' to C-6' and C-5 to C-8 may be unsubstituted or may independently be substituted by —OH, hydrocarbyl moieties, saccharide moieties and —$OR_{10}$; wherein $R_{10}$ is selected from the group consisting of hydrocarbyl moieties, acyl moeities and benzyl moieties, and wherein the hydrocarbyl moeities and the acyl moieties each contains from 1 to 10 carbon atoms, as well as such unsubstituted or substituted compounds in which the C-3 and C-4 carbons may have double bond between them to constitute a flavene as herein defined, and also such unsubstituted or substituted compounds in which the C-2 and C-3 carbon atoms are bonded by a double bond and the C-4 carbon together with an oxygen atom bonded thereto may be a carbonyl moiety to constitute a C-4 flavone, and also such unsubstituted or substituted compounds in which the C-2 and C-3 carbon atoms are bonded by a single bond and the C-3 or the C-4 carbons together with an oxygen atom bonded thereto may be a carbonyl moiety to constitute a C-3 or C-4 flavanone, and also such unsubstituted or substituted compounds in which the C-3 or the C-4 may have a hydroxy moiety bonded thereto so that the compound constitutes a C-3 or C-4 flavanol.

For purposes of this specification, the term "flavene" thus denotes a flavonoid compound of the general Formula (A):

Formula (A)

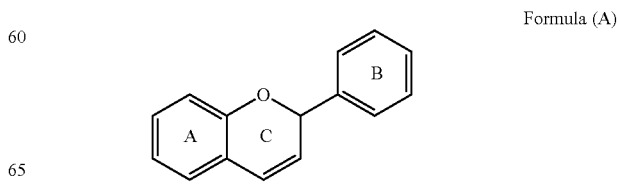

wherein the heterocyclic ring C of said flavonoid compound comprises a double bond between C-3 and C-4, and wherein the aromatic A- and B-rings may have a variety of different hydroxylation patterns and/or substituents, in particular H or OH, on one or more of the carbon atoms of said A- and B-rings.

The term "C-3 coupled biflavonoid" denotes a compound which is essentially a multimer (i.e. a dimer, trimer, tetramer etc.) of at least two monomeric units having flavonoid base structures and which are coupled together through a class 3 interflavanyl bond via the C-3 heterocyclic carbon.

The expression "C-3 coupled biflavonoid analogue" as used herein denotes a compound which is composed of at least two monomeric units, such that the first monomeric unit has a flavonoid base structure and the second monomeric unit has a non-flavonoid base structure, provided that said unit having a non-flavonoid base structure includes a nucleophilic aromatic moiety, and wherein the unit having a flavonoid base structure and the unit having a non-flavonoid base structure are coupled together through a class 3 interflavanyl bond via the C-3 heterocyclic carbon.

SUMMARY OF THE INVENTION

According to the present invention there is provided a method for the preparation of a compound which is selected from the group consisting of C-3 coupled biflavonoids and C-3 coupled biflavonoid analogues from a starting material or intermediate which is selected from the group consisting of flavan-3-ols and flavan-3-ones, the method comprising the steps of:
(a) providing a compound having a flavan-3-ol structure or a compound which is a flavan-3-one;
(b) if a compound having a flavan-3-ol structure with a hydroxy group on the C-3 carbon is selected as starting material, converting the hydroxy group on the C-3 carbon of the compound having the flavan-3-ol structure to an oxo group to form a flavan-3-one of that compound;
(c) providing a compound having a nucleophilic aromatic moiety, which compound is selected from the group of compounds having a nucleophilic aromatic moiety and which have flavonoid base structures and compounds having a nucleophilic aromatic moiety and which do not have a flavonoid base structure;
(d) contacting the flavan-3-one provided by step (a) or obtained by step (b) with the compound containing the nucleophilic aromatic moiety in the presence of a Lewis acid;
(e) forming a first intermediate compound wherein the oxo group on the C-3 carbon is converted to a hydroxy group by virtue of nucleophilic addition when the compound containing the nucleophilic aromatic moiety is contacted to the C-3 carbon of the flavan-3-one;
(f) subjecting the first, intermediate compound to dehydration so as to introduce a double bond between the C-3 carbon and C-4 carbon of the intermediate compound with the concomitant removal of the hydroxy group from the C-3 carbon to form a flavene compound which is substituted by the nucleophilic aromatic moiety on the C-3 carbon;
(g) optionally subjecting the resultant flavene compound to hydroboration-oxidation hydration thereby removing said double bond between the C-3 carbon and the C-4 carbon with the concomitant introduction of a hydroxy group at the C-4 carbon to form a second intermediate compound;
(h) further optionally oxidizing the second intermediate compound of step (g) thereby converting the hydroxy group at the said C-4 carbon to an oxo group, thereby forming a biflavonoid or biflavonoid analogue which is substituted by the selected nucleophilic aromatic moiety on the C-3 carbon;
(i) further optionally, and alternatively to step (h), subjecting the resultant flavene compound of step (f) to $OsO_4$ dihydroxylation thereby removing said double bond between the C-3 carbon and C-4 carbon with the concomitant introduction of a hydroxy group at the C-4 carbon and a hydroxy group at the C-3 carbon to form a third intermediate compound; and
(j) subjecting the third intermediate compound to dehydration whereby the hydroxy group at the C-3 carbon is removed and a double bond is introduced between the C-3 carbon and C-4 carbon thereby forming an enol product and allowing such enol product to rearrange spontaneously to form a biflavonoid or biflavonoid analogue having an oxo group at its C-4 carbon and which is substituted by the selected nucleophilic aromatic moiety on its C-3 carbon.

According to one form of the present invention the method is aimed at the preparation of optically active compounds of the identified class.

Thus, according to this form of the invention there is provided a method for the preparation of an optically active compound which is selected from the group consisting of C-3 coupled biflavonoids and C-3 coupled biflavonoid analogues from a starting material or intermediate which is selected from the group consisting of optically active flavan-3-ols and optically active flavan-3-ones, the method comprising the steps of:
(a) providing an optically active compound having a flavan-3-ol structure or a compound which is a flavan-3-one;
(b) if a compound having a flavan-3-ol structure with a hydroxy group on the C-3 carbon is selected as starting material, converting the hydroxy group on the C-3 carbon of the compound having the flavan-3-ol structure to an oxo group to form a flavan-3-one of that compound;
(c) providing a compound having a nucleophilic aromatic moiety, which compound is selected from the group of compounds having a nucleophilic aromatic moiety and which have flavonoid base structures and compounds having a nucleophilic aromatic moiety and which do not have a flavonoid base structure;
(d) contacting the flavan-3-one provided by step (a) or obtained by step (b) with the compound containing the nucleophilic aromatic moiety in the presence of a Lewis acid;
(e) forming a first intermediate compound wherein the oxo group on the C-3 carbon is converted to a hydroxy group by virtue of nucleophilic addition when the compound containing the nucleophilic aromatic moiety is contacted to the C-3 carbon of the flavan-3-one;
(f) subjecting, the first intermediate compound to dehydration so as to introduce a double bond between the C-3 carbon and C-4 carbon of the intermediate compound with the concomitant removal of the hydroxy group from the C-3 carbon to form an optically active flavene compound which is substituted by the nucleophilic aromatic moiety on the C-3 carbon;
(g) optionally subjecting the resultant flavene compound to hydroboration-oxidation hydration thereby removing said double bond between the C-3 carbon and the C-4 carbon with the concomitant introduction of a hydroxy group at the C-4 carbon to form a second intermediate compound;
(h) further optionally oxidizing the second intermediate compound of step (g) thereby converting the hydroxy group at the said C-4 carbon to an oxo group, thereby forming a biflavonoid or biflavonoid analogue which is substituted by the selected nucleophilic aromatic moiety on the C-3 carbon;
(i) further optionally, and alternatively to step (h), subjecting the resultant flavene compound of step (f) to OsO$_4$ dihydroxylation thereby removing said double bond between the C-3 carbon and C-4 carbon with the concomitant introduction of a hydroxy group at the C-4 carbon and a hydroxy group at the C-3 carbon to form a third intermediate compound; and
(j) subjecting the third intermediate compound to dehydration whereby the hydroxy group at the C-3 carbon is removed and a double bond is introduced between the C-3 carbon and C-4 carbon thereby forming an enol product and allowing such enol product to rearrange spontaneously to form a biflavonoid or biflavonoid analogue having an oxo group at its C-4 carbon and which is substituted by the selected nucleophilic aromatic moiety on its C-3 carbon.

According to one aspect of the invention there is provided a method for the preparation of an optically active C-3 coupled biflavonoid compound, the method comprising the steps of:
(a) providing an optically active compound having a flavan-3-ol structure;
(b) providing a compound having a nucleophilic aromatic moiety, which nucleophilic aromatic moiety has a flavonoid base structure;
(c) converting a hydroxy group on the C-3 carbon of the compound having the flavan-3-ol structure to an oxo group to form a flavan-3-one of that compound;
(d) contacting the flavan-3-one of that compound with the compound containing the nucleophilic aromatic moiety in the presence of a Lewis acid;
(e) forming a first intermediate compound wherein the oxo group on the C-3 carbon is converted to a hydroxy group by virtue of nucleophilic addition when the compound containing the nucleophilic aromatic moiety is contacted to the C-3 carbon of the flavan-3-one;
(f) subjecting the first intermediate compound to dehydration so as to introduce a double bond between the C-3 carbon and C-4 carbon of the intermediate compound with the concomitant removal of the hydroxy group from the C-3 carbon to form a flavene compound which is substituted by the nucleophilic aromatic moiety on the C-3 carbon;
(g) optionally subjecting the resultant flavene compound to hydroboration-oxidation hydration thereby removing said double bond between the C-3 carbon and the C-4 carbon with the concomitant introduction of a hydroxy group at the C-4 carbon to form a second intermediate compound;
(h) further optionally oxidizing the second intermediate compound thereby converting the hydroxy group at the said C-4 carbon to an oxo group, thereby forming a biflavonoid compound which is substituted by the nucleophilic aromatic moiety on the C-3 carbon;
(i) further optionally, and alternatively to step (h) subjecting the resultant flavene compound of step (g) to 0504 dihydroxylation thereby removing said double bond between the C-3 carbon and C-4 carbon with the concomitant introduction of a hydroxy group at the C-4 carbon and a hydroxy group at the C-3 carbon to form a third intermediate compound; and
(j) subjecting the third intermediate compound to dehydration whereby the hydroxy group at the C-3 carbon is removed and a double bond is introduced between the C-3 carbon and C-4 carbon thereby forming an enol product that will rearrange spontaneously to form a biflavonoid compound having an oxo group at its C-4 carbon and which is substituted by the nucleophilic aromatic moiety on its C-3 carbon.

According to another aspect of the present invention, there is provided a method of introducing a nucleophilic aromatic moiety onto a C-3 carbon of an optically active compound having a flavan-3-ol structure, comprising the steps of:
(a) converting a hydroxy group on the C-3 carbon of the compound having the flavan-3-ol structure to an oxo group to form a flavan-3-one of that compound;
(b) contacting a compound containing the nucleophilic aromatic moiety to the C-3 carbon of the flavan-3-one in the presence of Lewis acid;
(c) forming, an intermediate compound wherein the oxo group on the C-3 carbon is converted to a hydroxy group by virtue of nucleophilic addition when the compound containing the nucleophilic aromatic moiety is contacted to the C-3 carbon of the flavan-3-one; and
(d) subjecting the intermediate compound to dehydration so as to introduce a double bond between the C-3 carbon and C-4 carbon of the intermediate compound with the concomitant removal of the hydroxy group from the C-3 carbon to form a C-3-C-4 flavene compound which is substituted by the nucleophilic aromatic moiety on the C-3 carbon.

According to a further aspect of the invention, there is provided a method of preparing an optically active C-3-C-4 flavene compound having an aromatic substituent on its C-3 carbon comprising the steps of:
(a) providing an optically active compound having a flavan-3-ol structure;
(b) providing a compound having a nucleophilic aromatic moiety;
(c) converting a hydroxy group on the C-3 carbon of the compound having the flavan-3-ol structure to an oxo group to form a flavan-3-one of that compound;
(d) contacting the flavan-3-one of that compound with the compound containing the nucleophilic aromatic moiety in the presence of a Lewis acid;
(e) forming an intermediate compound wherein the oxo group on the C-3 carbon is converted to a hydroxy group by virtue of nucleophilic addition when the compound containing the nucleophilic aromatic moiety is contacted to the C-3 carbon of the flavan-3-one; and
(f) subjecting the intermediate compound to dehydration so as to introduce a double bond between the C-3 carbon and C-4 carbon of the intermediate compound with the concomitant removal of the hydroxy group from the C-3 carbon to form a C-3-C-4 flavene compound which is substituted by the nucleophilic aromatic moiety on the C-3 carbon.

According to a further aspect of the invention, there is provided a method for the preparation of an optically active C-3 coupled biflavonoid compound, the method comprising the steps of:
(a) providing an optically active compound having a flavan-3-ol structure;

(b) providing a compound having a nucleophilic aromatic moiety, which nucleophilic aromatic moiety has a flavonoid base structure;
(c) converting a hydroxy group on the C-3 carbon of the compound having the flavan-3-ol structure to an oxo group to form a flavan-3-one of that compound;
(d) contacting the flavan-3-one of that compound with the compound containing the nucleophilic aromatic moiety in the presence of a Lewis acid;
(e) forming a first intermediate compound wherein the oxo group on the C-3 carbon is converted to a hydroxy group by virtue of nucleophilic addition when the compound containing the nucleophilic aromatic moiety is contacted to the C-3 carbon of the flavan-3-one;
(f) subjecting the first intermediate compound to dehydration so as to introduce a double bond between the C-3 carbon and C-4 carbon of the intermediate compound with the concomitant removal of the hydroxy group from the C-3 carbon to form a flavene compound which is substituted by the nucleophilic aromatic moiety on the C-3 carbon;
(g) subjecting the resultant flavene compound to hydroboration-oxidation hydration thereby removing said double bond between the C-3 carbon and the C-4 carbon with the concomitant introduction of a hydroxy group at the C-4 carbon to form a second intermediate compound;
(h) oxidizing the second intermediate compound thereby converting the hydroxy group at the said C-4 carbon to an oxo group, thereby forming a biflavonoid compound which is substituted by the nucleophilic aromatic moiety on the C-3 carbon;
(i) alternatively subjecting the resultant flavene compound of step (g) to $OsO_4$ dihydroxylation thereby removing said double bond between the C-3 carbon and C-4 carbon with the concomitant introduction of a hydroxy group at the C-4 carbon and a hydroxy group at the C-3 carbon to form a third intermediate compound; and
(j) subjecting the third intermediate compound to dehydration whereby the hydroxy group at the C-3 carbon is removed and a double bond is introduced between the C-3 carbon and C-4 carbon thereby forming an enol product that will rearrange spontaneously to form a biflavonoid compound having an oxo group at its C-4 carbon and which, is substituted by the nucleophilic aromatic moiety on its C-3 carbon.

According to yet a further aspect of the invention, there is provided a method for the preparation of an optically active C-3 coupled biflavonoid analogue, the method comprising the steps of:
(a) providing an optically active compound having a flavan-3-ol structure;
(b) providing a compound having a nucleophilic aromatic moiety, which nucleophilic aromatic moiety does not have a flavonoid base structure;
(c) converting a hydroxy group on the C-3 carbon of the compound having the flavan-3-ol structure to an oxo group to form a flavan-3-one of that compound;
(d) contacting the flavan-3-one of that compound with the compound containing the nucleophilic aromatic moiety in the presence of a Lewis acid;
(e) forming a first intermediate compound wherein the oxo group on the C-3 carbon is converted to a hydroxy group by virtue of nucleophilic addition when the compound containing the nucleophilic aromatic moiety is contacted to the C-3 carbon of the flavan-3-one;

(f) subjecting the first intermediate compound to dehydration so as to introduce a double bond between the C-3 carbon and C-4 carbon of the intermediate compound with the concomitant removal of the hydroxy group from the C-3 carbon to form a flavene compound which is substituted by the nucleophilic aromatic moiety on the C-3 carbon;
(g) subjecting the resultant flavene compound to hydroboration-oxidation hydration thereby removing said double bond between the C-3 carbon and the C-4 carbon with the concomitant introduction of a hydroxy group at the C-4 carbon to form a second intermediate compound;
(h) oxidizing the second intermediate compound thereby converting the hydroxy group at the said C-4 carbon to an oxo group, thereby forming a biflavonoid analogue which is substituted by the nucleophilic aromatic moiety on the C-3 carbon;
(i) alternatively subjecting the resultant flavene compound of step (g) to $OsO_4$ dihydroxylation thereby removing said double bond between the C-3 carbon and C-4 carbon with the concomitant introduction of a hydroxy group at the C-4 carbon and a hydroxy group at the C-3 carbon to form a third intermediate compound; and
(j) subjecting the third intermediate compound to dehydration whereby the hydroxy group at the C-3 carbon is removed and a double bond is introduced between the C-3 carbon and C-4 carbon thereby forming an enol product that will rearrange spontaneously to form a biflavonoid analogue having an oxo group at its C-4 carbon and which is substituted by the nucleophilic aromatic moiety on its C-3 carbon.

According to a specific application of the present invention, there is provided a method for the preparation of an optically active 3-aryl-flav-3-ene, the method comprising the steps of:
(a) providing an optically active 3-oxo-derivative of a flavan-3-ol, represented by Formula (I) (hereinafter referred to as "the 3-oxo-derivative"):

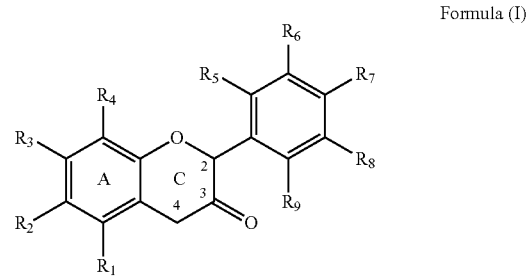

Formula (I)

wherein
each of $R_1$, $R_2$, $R_3$, $R_4$, $R_5$, $R_6$, $R_7$, $R_8$ and $R_9$ is independently selected from the group consisting of —H, —OH, hydrocarbyl groups, saccharide moieties and —$OR_{10}$;
wherein $R_{10}$ is selected from the group consisting of a hydrocarbyl group, an acyl group and a benzyl group; and
wherein, the hydrocarbyl groups in any one of $R_1$ to $R_{10}$ and the acyl group contains from 1 to 10 carbon atoms;
(b) providing a compound having a nucleophilic aromatic moiety;

(c) contacting the 3-oxo-derivative with the compound containing the nucleophilic aromatic moiety in the presence of a Lewis acid;
(d) forming an intermediate compound wherein the oxo group on the C-3 carbon of the 3-oxo-derivative is converted to a hydroxy group by virtue of nucleophilic addition when the compound containing the nucleophilic aromatic moiety is contacted to the C-3 carbon of said 3-oxo-derivative; and
(e) subjecting the intermediate compound to dehydration so as to introduce a double bond between the C-3 carbon and C-4 carbon of the intermediate compound with the concomitant removal of the hydroxy group from the said C-3 carbon to form a 3-aryl-flav-3-ene which is substituted by the nucleophilic aromatic moiety on the C-3 carbon.

According to a further specific application of the present invention, there is provided a method for the preparation of an optically active I-3, II-6/8 biflavonoid and/or a I-3, II-6/8 biflavonoid polymer, the method comprising the steps of:
(a) providing an optically active 3-oxo-derivative represented by Formula (I) provided hereinabove:
  wherein
    each of $R_1$, $R_2$, $R_3$, $R_4$, $R_5$, $R_6$, $R_7$, $R_8$ and $R_9$ is independently selected from the group consisting of —H, —OH, hydrocarbyl groups, saccharide moieties and —$OR_{10}$;
    wherein $R_{10}$ is selected from the group consisting of a hydrocarbyl group, an acyl group and a benzyl group; and
    wherein the hydrocarbyl groups in any one of $R_1$ to $R_{10}$ and the acyl group contains from 1 to 10 carbon atoms;
(b) providing a compound having a nucleophilic aromatic moiety, which nucleophilic aromatic, moiety has a flavonoid base structure;
(c) contacting the 3-oxo-derivative with the compound containing the nucleophilic aromatic moiety in the presence of a Lewis acid;
(d) forming a first intermediate compound wherein the oxo group on the C-3 carbon of the 3-oxo-derivative is converted to a hydroxy group by virtue of nucleophilic addition when the compound containing the nucleophilic aromatic moiety is contacted to the C-3 carbon of said 3-oxo-derivative;
(e) subjecting the first intermediate compound to dehydration so as to introduce a double bond between the C-3 carbon and C-4 carbon of the intermediate compound with the concomitant removal of the hydroxy group from the said C-3 carbon to form a 3-aryl-flav-3-ene which is substituted by the nucleophilic aromatic moiety on the C-3 carbon;
(f) subjecting the resultant 3-aryl-flav-3-ene to hydroboration-oxidation hydration thereby removing said double bond between the C-3 carbon and the C-4 carbon with the concomitant introduction of a hydroxy group at the C-4 carbon to form a second intermediate compound;
(g) oxidizing the second intermediate compound thereby converting the hydroxy group at the said C-4 carbon to an oxo group, thereby forming a I-3, II-6/8 biflavonoid compound which is substituted by the nucleophilic aromatic moiety on the C-3 carbon;
(h) alternatively subjecting the resultant 3-aryl-flav-3-ene of step (e) to $OsO_4$ dihydroxylation, thereby removing said double bond between the C-3 carbon and C-4 carbon with the concomitant introduction of a hydroxy group at the C-4 carbon and a hydroxy group at the C-3 carbon to form a third intermediate compound;
(i) subjecting the third intermediate compound to dehydration whereby the hydroxy group at the C-3 carbon is removed and a double bond is introduced between the C-3 carbon and C-4 carbon thereby forming an enol product that will rearrange spontaneously to form a I-3, II-6/8 biflavonoid compound having an oxo group at its C-4 carbon and which is substituted by the nucleophilic aromatic moiety on its C-3 carbon;
(j) optionally, and where a hydroxy group at the C-3 position of the compound containing the nucleophilic aromatic moiety has been converted to an oxo group by means of the oxidation in step (g) (hereinafter referred to as "the secondary 3-oxo-derivative" of the I-3, II-6/8 biflavonoid), providing an additional compound which has a nucleophilic aromatic moiety (hereinafter referred to as "the additional compound");
(k) contacting the secondary 3-oxo-derivative with the additional compound in the presence of a Lewis acid; and
(l) optionally repeating the steps (d), (e), (f), (g), (h) and (i) as many times as is necessary to achieve the incorporation of the desired number of monomeric units in the resultant I-3, II-6/8 biflavonoid polymer.

According to a yet further specific application of the present invention, there is provided a method for the preparation of an optically active I-3, II-6/8 biflavonoid analogue, the method comprising the steps of:
(a) providing an optically active 3-oxo-derivative represented by Formula (I) provided hereinabove:
  wherein
    each of $R_1$, $R_2$, $R_3$, $R_4$, $R_5$, $R_6$, $R_7$, $R_8$ and $R_9$ is independently selected from the group consisting of —H, —OH, hydrocarbyl groups, saccharide moieties and —$OR_{10}$;
    wherein $R_{10}$ is selected from the group consisting of a hydrocarbyl group, an acyl group and a benzyl group; and
    wherein the hydrocarbyl groups in any one of $R_1$ to $R_{10}$ and the acyl group contains from 1 to 10 carbon atoms;
(b) providing a compound having a nucleophilic aromatic moiety, which nucleophilic aromatic moiety does not have a flavonoid base structure;
(c) contacting the 3-oxo-derivative with the compound containing the nucleophilic aromatic moiety in the presence of a Lewis acid;
(d) forming a first intermediate compound wherein the oxo group on the C-3 carbon of the 3-oxo-derivative is converted to a hydroxy group by virtue of nucleophilic addition when the compound containing the nucleophilic aromatic moiety is contacted to the C-3 carbon of said 3-oxo-derivative;
(e) subjecting the first intermediate compound to dehydration so as to introduce a double bond between the C-3 carbon and C-4 carbon of the intermediate compound with the concomitant removal of the hydroxy group from the said C-3 carbon to form a 3-aryl-flav-3-ene which is substituted by the nucleophilic aromatic moiety on the C-3 carbon;
(f) subjecting the resultant 3-aryl-flav-3-ene to hydroboration-oxidation hydration thereby removing said double bond between the C-3 carbon and the C-4 carbon with the concomitant introduction of a hydroxy group at the C-4 carbon to form a second intermediate compound;

(g) oxidizing the second intermediate compound thereby converting the hydroxy group at the said C-4 carbon to an oxo group, thereby forming a I-3, II-6/8 biflavonoid analogue which is substituted by the nucleophilic aromatic moiety on the C-3 carbon;

(h) alternatively subjecting the resultant 3-aryl-flav-3-ene of step (e) to $OsO_4$ dihydroxylation, thereby removing said double bond between the C-3 carbon and C-4 carbon with the concomitant introduction of a hydroxy group at the C-4 carbon and a hydroxy group at the C-3 carbon to form a third intermediate compound; and (i) subjecting the third intermediate compound to dehydration whereby the hydroxy group at the C-3 carbon is removed and a double bond is introduced between the C-3 carbon and C-4 carbon thereby forming an enol product that will rearrange spontaneously to form a I-3, II-6/8 biflavonoid analogue having an oxo group at its C-4 carbon and which is substituted by the nucleophilic aromatic moiety on its C-3 carbon.

It will be appreciated by the skilled person that the stereochemistry at C-2 of the compound of Formula (I) allows for the products of Formula (I) to exist in alpha or beta form. It will be further appreciated that the aforesaid stereochemistry of the compound of Formula (I) affords optically active products which may be enantiomerically pure. Also the stereochemistry at the C-2 carbon determines the stereochemistry at the C-3 carbon of the final product.

It will further be appreciated that all the aspects of the present invention relating to the preparation of optically active products from optically active starting materials as described above apply equally to the preparation of optically inactive products by utilising optically inactive starting materials, such as racemic mixtures of the selected starting materials. The aspects of the invention in so far as they relate to the preparation of optically active products from optically active starting materials are thus to be read mutatis mutandis as applicable to the preparation of optically inactive products by starting with optically inactive starting materials.

The 3-oxo-derivative of flavan-3-ol may be prepared from a flavan-3-ol wherein the hydroxy group at the 3 position of the flavan-3-ol is oxidised to an oxo group. This may be achieved by any means known in the art. Such preparation may, for example, be effected by the procedure known as Dess-Martin oxidation.

The hydrocarbyl groups from which $R_1$-$R_{10}$ may be selected may be linear hydrocarbyl groups or cyclic hydrocarbyl groups.

The linear hydrocarbyl groups may be selected from the group consisting of methyl, ethyl, propyl, butyl, pentyl, hexyl, heptyl, octyl, nonyl, and decyl.

The cyclic hydrocarbyl may be selected from the group consisting of cyclopropyl, cyclobutyl, cyclopentyl, cyclohexyl, cycloheptyl, cyclooctyl, cyclononyl, and cyclodecyl.

The hydrocarbyl groups from which $R_{10}$ may be selected are preferably a benzyl group or an acyl group.

The saccharide moieties may be selected from the group consisting of monosaccharides, disaccharides, oligosaccharides, polysaccharides and analogues of these saccharides.

The compound having a nucleophilic aromatic moiety may be a compound having a protected or unprotected phenolic, flavanyl or flavonoid moiety.

Where the compound having a nucleophilic aromatic moiety is a compound having a phenolic moiety (hereinafter referred to as the "phenolic species"), the phenolic moiety is preferably a protected phenolic moiety. In a preferred embodiment of the invention, the phenolic species is 1,3,5-tri-O-methylphloroglucinol. The coupling of the 3-oxo-derivative and the phenolic species results in the formation of a 3-aryl-flav-3-ene comprising the 3-oxo-derivative and the phenolic moiety. Hydroboration-oxidation hydration, followed by oxidation of the resulting 3-aryl-4-hydroxy-flavane results in the formation of a C-3 coupled biflavonoid analogue which is substituted by the phenolic moiety on the C-3 carbon. Alternatively, $OsO_4$ or similar dihydroxylation of the 3-aryl-flav-3-ene followed by dehydration of the resulting 3,4-dihydroxy-3-aryl-flavane results in the formation of a C-3 coupled biflavonoid analogue substituted by the phenolic moiety on the C-3 carbon.

Where the compound having a nucleophilic aromatic moiety is a compound having a flavanyl or flavonoid moiety, the compound containing said flavanyl or flavonoid moiety (hereinafter referred to as the "flavanol species") is preferably flavan-3-ol, most preferably 5,7,3',4'-tetrakis(methyloxy)flavan-3-one. The coupling of the 3-oxo-derivative and the flavanol species results in the formation of a 3-aryl-flav-3-ene comprising the 3-oxo-derivative and the flavanol or flavonoid moiety. Hydroboration-oxidation hydration, followed by oxidation of the resulting 3-aryl-flav-3-ene results in the formation of a C-3 coupled biflavonoid compound which is substituted by the flavanol or flavonoid moiety on the C-3 carbon. Alternatively, $OsO_4$ or similar dihydroxylation of the 3-aryl-flav-3-ene followed by dehydration results in the formation of a C-3 coupled biflavonoid compound substituted by the flavanol or flavonoid moiety on the C-3 carbon.

It will be appreciated by the person skilled in the art that compounds having other suitable nucleophilic aromatic moieties may be used without departing from the spirit and scope of the invention.

The compound having the nucleophilic aromatic moiety, as described herein above, is coupled to the 3-oxo-derivative through a class 3 interflavanyl bond via the C-3 heterocyclic carbon atom.

Hydroboration-oxidation hydration, employed in the methods provided hereinabove, converts the double bond between the C-3 carbon and the C-4 carbon in the C ring of the flavene compound into the corresponding alcohol by the addition of water across the double bond. It is envisaged that hydroboration-oxidation hydration as well as dihydroxylation, particularly $OsO_4$ dihydroxylation, will be employed to obtain a hydroxy group in the C-4 position.

The resultant flavene compound and the resultant biflavonoid compound may be further derivatised by replacing the hydroxy substituents on the C-3 nucleophilic aromatic moiety with any other substituent. Thus the resultant compound may be acetylated to convert the hydroxy groups to acetate groups.

The Lewis agent may be selected from the group consisting of $SnCl_4$, $TiCl_4$, $InCl_3$ and $Yb(OTF)_3$. In a preferred embodiment of the invention, the Lewis acid is $SnCl_4$.

The compound having a nucleophilic aromatic moiety, the 3-oxo-derivative and the Lewis acid may be mixed together in the presence of a solvent. The solvent may be any suitable aprotic solvent that is capable of dissolving said compound and the 3-oxo-derivative that are to be coupled. Preferably, the solvent is dichloromethane.

In a preferred embodiment of the invention, $R_1$, $R_3$, $R_6$ and $R_7$ are the same and $R_2$, $R_4$, $R_5$, $R_8$ and $R_9$ are H. Preferably each of $R_1$, $R_3$, $R_6$ and $R_7$ are $OR_{10}$, wherein $R_{10}$ is —$CH_3$ and C-2 is in the (2R) configuration. In such a case, the 3-oxo-derivative is tetra-O-methyl-3-oxo-catechin represented by Formula (II)

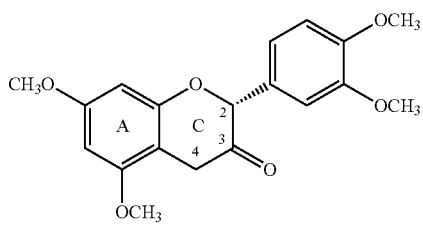

By oxidising the flavan-3-ol to the 3-oxo-derivative, the reactivity of the benzene ring "A" in Formula (II) is decreased to such a degree that self-condensation between atoms of the 3-oxo-derivative is avoided. This, in turn, allows for the isolation of the flavene compound and/or the C-3 coupled biflavonoid compound, or the C-3 coupled biflavonoid analogue, as the case may be, that forms when the 3-oxo derivative couples to the nucleophilic aromatic moiety of the compound, as discussed herein above.

Where the nucleophilic aromatic moiety, in the form of a protected phenolic species—preferably 1,3,5-tri-O-methylphloroglucinol, is contacted with the 3-oxo-derivative of Formula (II), the resulting flavene is represented by Formula (III):

Formula (III)

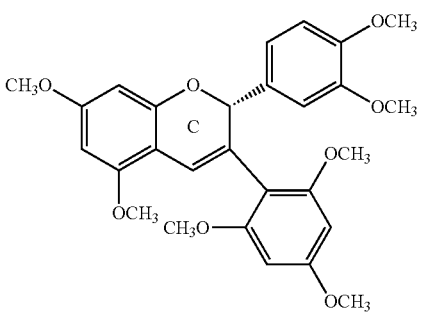

Where the flavene represented by Formula (III) is subjected to hydroboration-oxidation hydration followed by oxidation, or where the flavene represented by Formula (III) is subjected to OsO$_4$ dihydroxylation followed by dehydration, the resulting C-3 coupled biflavonoid analogue is represented by Formula (IVa) and Formula (IVb), whereby Formula (IVa) and Formula (IVb) represent the beta and alpha stereochemistry at C-3, respectively:

Formula (IVa)

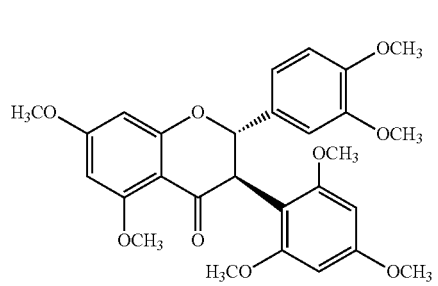

Formula (IVb)

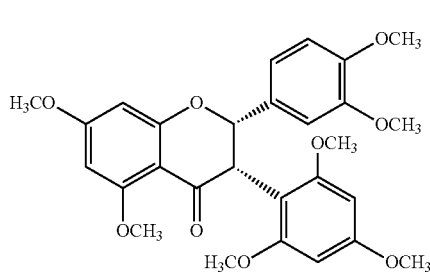

Where the nucleophilic aromatic moiety, in the form of flavan-3-ol—preferably 5,7,3',4'-tetrakis(methyloxy)flavan-3-one, is contacted with the 3-oxo-derivative of Formula (II), the resulting flavene is represented by Formula (V):

Formula (V)

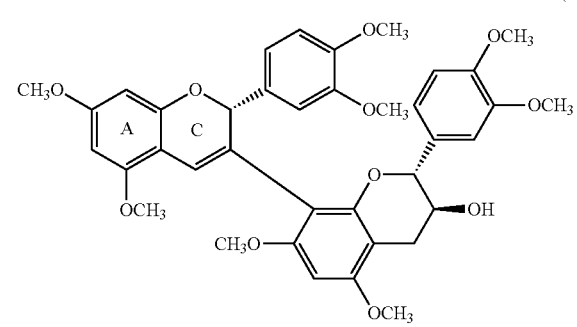

Where the flavene represented by Formula (V) is subjected to hydroboration-oxidation hydration followed by oxidation or where the flavene represented by Formula (V) is subjected to OsO$_4$ dihydroxylation followed by dehydration, the resulting C-3 coupled biflavonoid compound is represented by Formula (VIa) and Formula (VIb), whereby Formula (VIa) and Formula (VIb) represent the beta and alpha stereochemistry at C-3, respectively:

Formule (VIa)

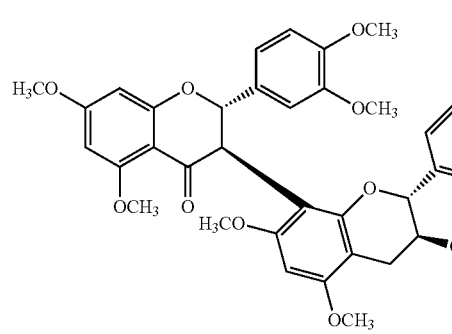

Formule (VIb)

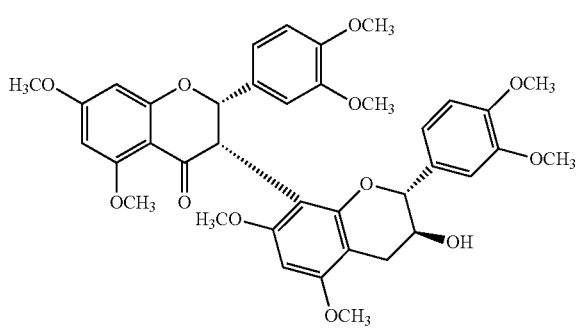

Where the 3-oxo-derivative employed in the present invention contains reactive substituent groups that are prone to be reacted by the oxidation step, such reactive substituent groups may be protected before the oxidation step is performed, and such protective groups may be removed to restore the original substituent groups, if required.

The invention further provides for the flavanyl moiety in the resulting C-3 coupled biflavonoid compound of Formula (VIa) and Formula (VIb) to be oxidised so as to convert the hydroxy group at C-3 to an oxo group as represented in Formula (VIIa) and Formula (VIIb), whereby Formula (VIIa) and Formula (VIIb) represent the beta and alpha stereochemistry at C-3, respectively:

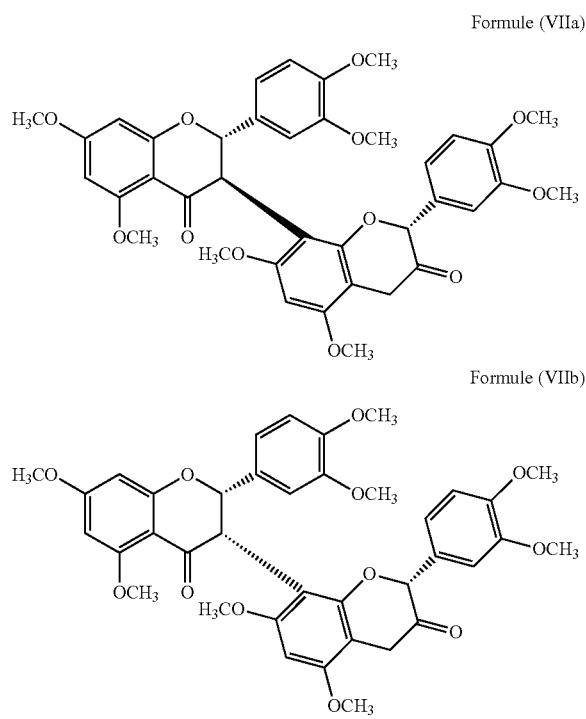

The invention further provides for the C-3 coupled biflavonoid compound of Formula (VIIa) and Formula (VIIb) to be contacted with a further compound having a nucleophilic aromatic moiety, of the type described herein above, in the presence of a Lewis acid, preferably $SnCl_4$, as herein before described. Where the further compound having the nucleophilic aromatic moiety is a flavanol species, coupling of this flavanol species to the biflavonoid compound of Formula (VIIa) and Formula (VIIb) yields a trimer in which the constituent units are coupled by means of a class 3 interflavanyl bond via the C-3 heterocyclic carbon atom:

According to a further embodiment of the invention and where $R_{10}$ is a benzyl group, hydrogenation may be employed after coupling so as to remove the benzyl groups. Where $R_{10}$ is acetate, said acetate may be removed by means of a weak acid or base. In this way, free phenolic flavenes, C-3 coupled biflavonoid compounds and C-3 coupled biflavonoid analogues may be produced.

According to a further embodiment of the present invention, the hydroxy group at the C-3 position of the flavanyl moiety of the C-3 coupled biflavonoid compound of Formula (VI) may be dehydrated (via mesylation followed by treatment with DBU) to yield a C-3 coupled biflavonoid compound with a flav-3-ene moiety, as represented in Formula (VIIIa) and Formula (VIIIb), whereby Formula (VIIIa) and Formula (VIIIb) represent the beta and alpha stereochemistry at C-3, respectively:

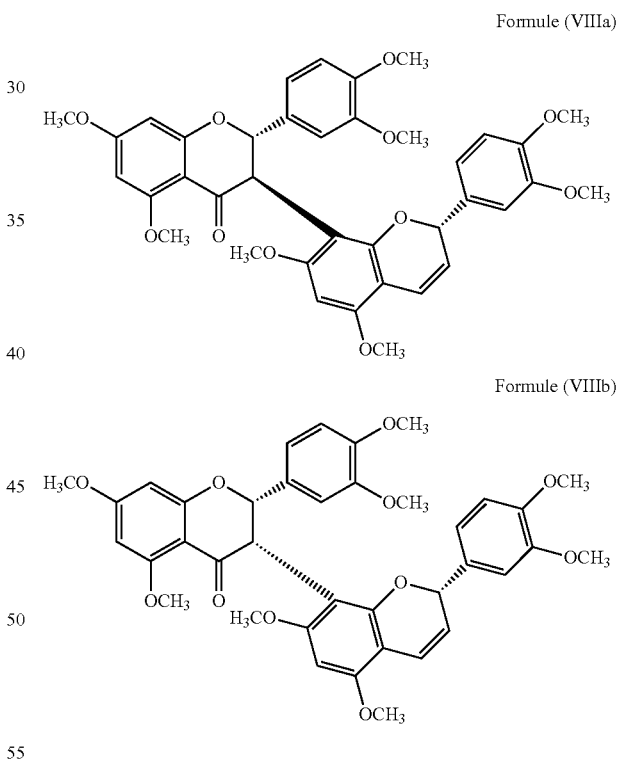

Where the flav-3-ene moiety in Formula (VIIIa) and Formula (VIIIb) is subjected to hydration followed by oxidation or where the said flav-3-ene moiety is subjected to $OsO_4$ dihydroxylation followed by dehydration, the resulting C-3 coupled biflavonoid compound is represented by Formula (IXa) and Formula (IXb), whereby Formula (IXa) and Formula (IXb) represent the beta and alpha stereochemistry at C-3, respectively. This compound belongs to the GB series of biflavonoids. Similar results may be obtained by using a flavanone as the compound with the nucleophilic aromatic moiety.

Formule (IXa)

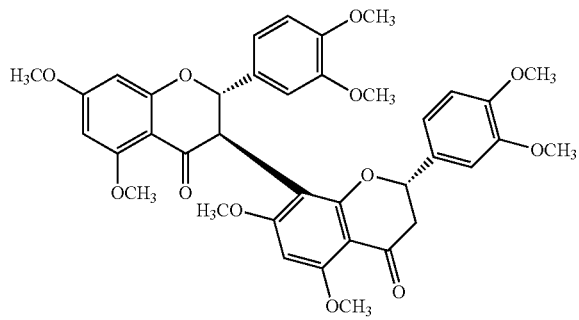

Formule (IXb)

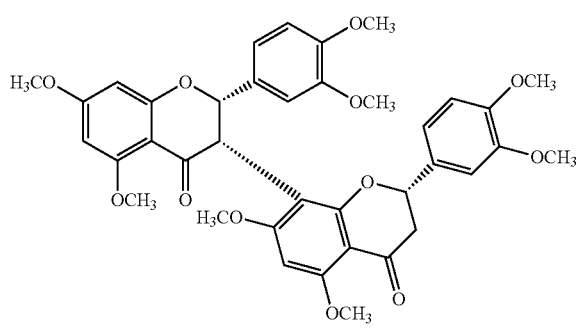

In a further embodiment of the invention, a flavone according to Formula (X) may be used as the compound with the nucleophilic aromatic moiety. Morelloflavone (4), for example, can be obtained, after deprotection, in this way.

Formule (X)

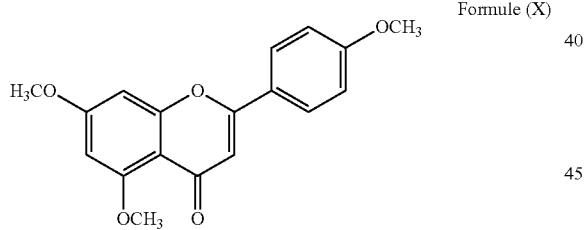

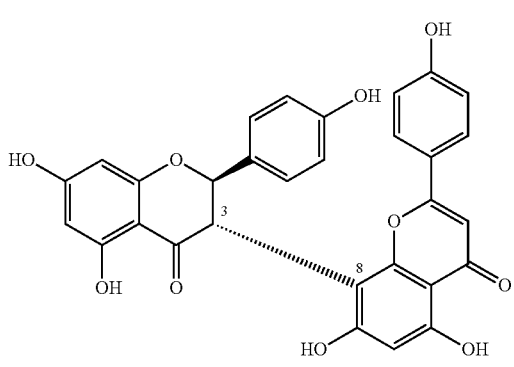

Morelloflavone

These and other features of the invention are described in more detail below.

EXAMPLES OF THE INVENTION

The invention will now be described with reference to the following non-limiting example.
General Information:
NMR Spectra
NMR experiments were carried out on a Brucker Avance spectrometer (600 MHz). SiMe$_4$ was added as reference to all NMR samples.
Abbreviations of TLC solvents: EtOAc=ethyl acetate, H=hexane, DMSO=dimethylsulfoxide.

Example 1

Preparation of 3-arylflav-3-ene

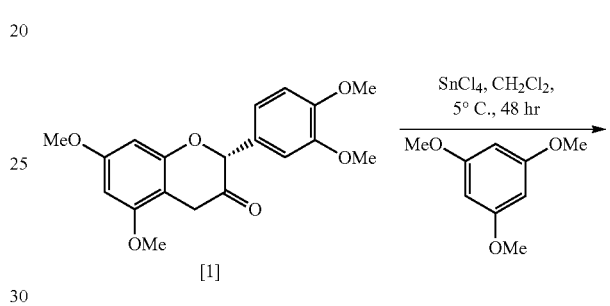

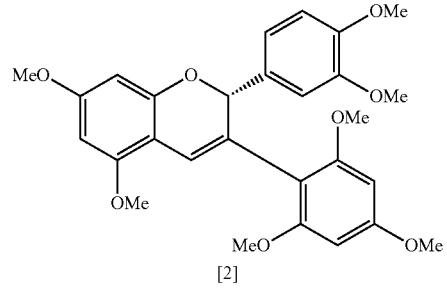

Dried (2R)-5,7,3',4'-tetrakis(methyloxy)flavan-3-one [1] (100 mg, 0.29 mmol) and 1,3,5-tri-O-methylphloroglucinol (120 mg, 0.710 mmol, 2.5 eq.) were dissolved in dry dichloromethane (10 mL) and the mixture was cooled in ice/NaCl bath. Tin(IV)chloride (1 M solution in dichloromethane, 0.5 mL, 0.5 mmol, 1.7 eq.) was added dropwise to the solution and the reaction mixture was stirred under argon in thawing ice/NaCl bath for 24 hours (TLC monitoring of consumption of starting materials). The reaction mixture was filtered on a basic aluminum oxide pack and washed with ethyl acetate. Purification on silica preparative TLC plates afforded 3-(1,3,5-O-methylphloroglucinol)-5,7,3',4'-tetramethoxyflavan-3-ene [2] (R$_f$ 0.26, 70.2 mg, 49%).

$^1$H NMR: δ (DMSO) 3.64-3.80 (s, 21H, 7×OCH$_3$), 5.83 (br, 1H, 4-H), 6.03 (br s, 1H, 2-H), 6.26 (s, 2H, 3"/5"-H), 6.33 (d, J=2.0 Hz, 1H, 6-H), 6.69 (dd, J=0.6, 2.0 Hz, 1H, 8-H), 6.78 (dd, J=2.0, 8.3 Hz, 1H, 6'-H), 6.85 (d, J=8.3 Hz, 1H, 5'-H), 6.90 (d, J=2.0 Hz, 1H, 2'-H).

$^{13}$C NMR: δ (DMSO) 40.52 (C-4), 55.67-56.30 (7×OCH$_3$), 88.95 (C-8), 92.11 (C-3"/5"), 94.23 (C-6), 100.10 (C-2), 110.35 (C-1"), 111.98 (C-5'), 112.07 (C-10), 113.16

(C-2), 121.26 (C-6), 134.00 (C-1'), 155.91 (C-9), 158.70 (C-3), 147.85-152.75, 158.34, 158.97, 160.49 (7×C—OCH₃).

MS-ESI: 495.6 (M⁺+H), 327.6 (495.6—C₆H₃(OMe)₃).

Example 2

Preparation of 3-arylflav-4-one

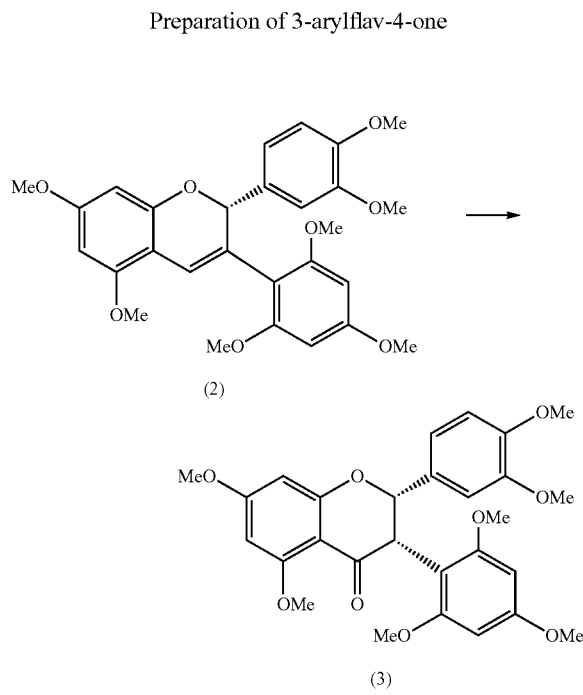

3-(1,3,5-O-methoxyphloroglucinol)-5,7,3',4'-tetramethoxyflavan-3-ene (2) (50 mg, 0.10 mmol) was dissolved in THF (5 mL) and OsO₄ (3.1 mg, 0.012 mmol) and N-methylmorpholine-N-oxide (56.2 mg, 0.48 mmol) was added. The reaction mixture is stirred 1-2 days at r.t. under argon (TLC monitoring of consumption of starting material). Solution of sodium metabisulfite (10% aq.) was added and reaction mixture was stirred for 30 minutes. Then was made the extraction 3× with dichloromethane, washed with NaHCO₃ (sat. aq.), NaCl (sat. aq.) and dried over MgSO₄. Evaporation left crude material which was purified on preparative TLC plates to afford 3-(1,3,5-O-methoxyphloroglucinol)-5,7,3',4'-tetramethoxyflavan-4-one (3) (15 mg, 0.29 mmol, 29%).

¹H NMR: δ (CDCl₃) 3.35 (s, 3H, 4''-OMe), 3.63 (s, 6H, 2''/6''-OMe), 3.77 (s, 3H, OMe), 3.80 (s, 3H, OMe), 3.81 (s, 3H, OMe), 3.82 (s, 3H, OMe), 5.08 (s, 1H, 6-H), 5.52 (s, 1H, 8-H), 5.85 (d, J=2.3 Hz, 1H, 3-H), 6.07 (s, 2H, 2''/5''-H), 6.10 (d, J=2.2 Hz, 2-H), 6.05 (dd, J=4.2, 1.9 Hz, 6'-H), 6.74 (d, J=10.9 Hz, 5'-H), 6.74 (s, 1H, 6'-H).

¹³C NMR: δ (CDCl₃) 48.83 (C-3), 55.69-56.32 (7×OCH₃), 70.39 (C-2), 90.46 (C-3''/5''), 90.76 (C-6), 94.21 (C-8), 104.90 (C-1''), 107.67 (C-1'), 110.82 (C-4'), 131.14 (C-2'), 121.43 (C-5'), 130.57 (C-10), 147.82, 148.37, 157.61, 158.47, 158.80, 160.92, 161.71 (7×C—OCH₃), 211.06 (C=O).

MS-ESI: 511.8 ((M⁺+H), 343.66 (411.8—C₆H₃(OMe)₃).

Example 3

Preparation of (2R)-3-[(2R,3S)-5,7,3',4'-tetrakis(methyloxy)-3-hydroxyflavan)]-5,7,3',4'-tetramethoxyflavan-3-ene (6)

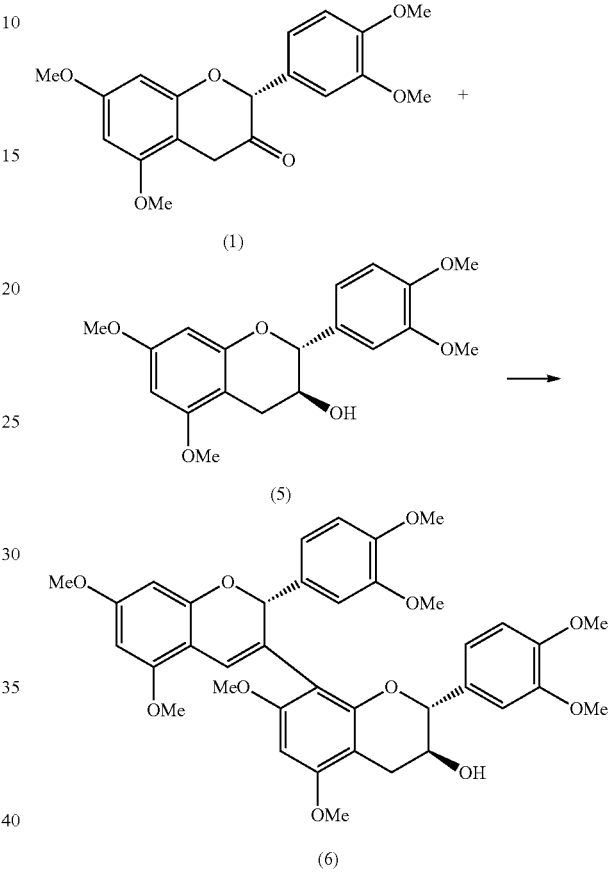

Dried (2R)-5,7,3',4'-tetrakis(methyloxy)flavan-3-one (1) (200 mg, 0.581 mmol) and (2R,3S)-5,7,3',4'-tetrakis(methyloxy)flavan-3-ol (5) (400 mg, 1.162 mmol, 2 eq.) was dissolved in dry dichloromethane (10 mL) and the mixture was cooled in ice/NaCl bath. Then tin(IV)chloride (1 M solution in dichloromethane, 1 mL, 1 mmol, 1.7 eq.) was added dropwise and the reaction mixture was stirred under argon in thawing ice/NaCl bath for 24 hours (TLC monitoring of consumption of starting materials). The reaction mixture was then filtered on a basic aluminium oxide and washed with ethyl acetate. Purification on silica preparative TLC plates (hexane-ethyl acetate 4:6) afforded (2R)-3-[(2R,3S)-5,7,3',4'-tetrakis(methyloxy)-3-hydroxyflavan)]-5,7,3',4'-tetramethoxyflavan-3-ene (6) (Rf 0.20, 40.1 mg, 0.060 mmol, 10%).

¹H NMR: δ (CDCl₃) 2.54-2.64 (m, 1H, 4''-H), 3.05-3.15 (m, 1H, 4''-H), 3.45-3.94 (m, 24H, 8×OMe), overlapped—4.00 (m, 1H, 2''-H), 4.42 (dd, J=25.6, 8.5 Hz, 1H, 3''-H), 5.94+6.00 (2×s, 1H, rotamer, 2-H), 6.05-6.25 (2×s, 1H, rotamer, 4-H), 6.18-6.95 (s+m, 9H, rotamers, aromatics).

¹³C NMR: (CDCl₃) δ7.0 (C-4''), 48.25 (C-2), 53-57 (8×OCH₃), 58.1 (C-2''), 82.5 (C-3''), 88.14 (C-6/8), 94

(C-6″), 100.0 (C-4), 105.14-125.02 (C-2′, C-5′, C-6′, C-2‴, C-6‴), 147.56-160.01 (8×C—OCH₃),

MS-ESI: 673.6 (M⁺+H), 327.5 (673.6—C₉H₉OH (OMe)₄).

Example 4

Preparation of (2S,3S)-3-[(2R,3S)-5,7,3′,4′-tetrakis(methyloxy)-3-hydroxyflavan)]-5,7,3′,4′-tetramethoxyflavan-3-one (7)

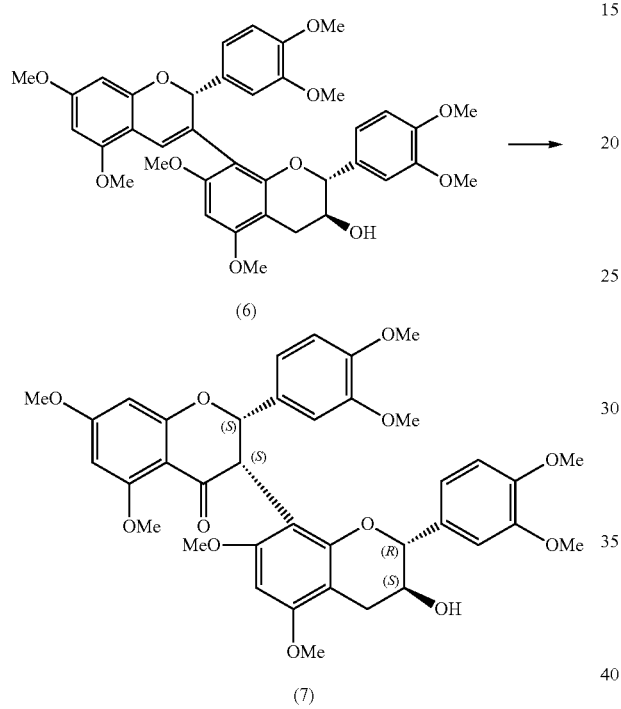

(2R)-3-[(2R,3S)-5,7,3′,4′-tetrakis(methyloxy)-3-hydroxyflavan)]-5,7,3′,4′-tetramethoxyflavan-3-ene (6) (20 mg, 0.030 mmol) was dissolved in THF (5 mL) and OsO₄ (0.9 mg, 0.004 mmol) and N-methylmorpholine-N-oxide (16.3 mg, 0.139 mmol) was added. The reaction mixture is stirred 1-2 days at r.t. under argon (TLC monitoring of consumption of starting material). Solution of sodium metabisulfite (10% aq.) was added and reaction mixture was stirred for 30 minutes. Then was made the extraction 3× with dichloromethane, washed with NaHCO₃ (sat. aq.), NaCl (sat. aq.) and dried over MgSO₄. Evaporation left crude material which was purified on preparative TLC plates (toluene acetone 6:4) to afford (2S,3S)-3-[(2R,3S)-5,7,3′,4′-tetrakis(methyloxy)-3-hydroxyflavan)]-5,7,3′,4′-tetramethoxyflavan-3-one (7) (Rf 0.19, 6 mg, 0.009 mmol, 30%).

The invention claimed is:

1. A method for the preparation of a compound selected from the group consisting of C-3 coupled bioflavonoid compounds and C-3 coupled biflavonoid analogues from flavan-3-ols or flavan-3-ones, the method comprising the steps of:

(a) providing a flavan-3-one of Formula (I) or a corresponding flavan-3-ol:

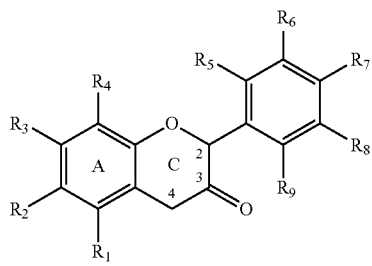

wherein
each of $R_1$, $R_2$, $R_3$, $R_4$, $R_5$, $R_6$, $R_7$, $R_8$ and $R_9$ is independently selected from the group consisting of hydrogen, —OH, a hydrocarbyl group; a saccharide moiety and —$OR_{10}$; wherein $R_{10}$ is selected from the group consisting of a hydrocarbyl group, an acyl group and a benzyl group; and wherein, the hydrocarbyl group in any one of $R_1$ to $R_{10}$ and/or the acyl group contains from 1 to 10 carbon atoms;

(b) optionally, converting the C-3 hydroxy group of the flavan-3-ol to an oxo group to form the flavan-3-one;

(c) providing a compound having a nucleophilic aromatic moiety, selected from the group consisting of a flavonoid base structure:

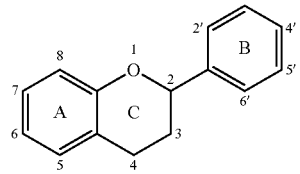

wherein
carbon C-3 is optionally substituted with —OH; and
carbons C-2′ to C-6′ and C-5 to C-8 are unsubstituted or independently substituted with —OH, a saccharide moiety, $R_{11}$, $OR_{11}$ or O—C(O)—$R_{12}$, wherein $R_{11}$ is a linear hydrocarbyl group selected from the group consisting of methyl, ethyl, propyl, butyl, pentyl, hexyl, heptyl, octyl, nonyl, and decyl, or wherein $R_{11}$ is a cyclic hydrocarbyl group selected from the group consisting of cyclopropyl, cyclobutyl, cyclopentyl, cyclohexyl, cycloheptyl, cyclooctyl, cyclononyl, and cyclodecyl, or wherein $OR_{11}$ is O-benzyl;

wherein $R_{12}$ is a linear hydrocarbyl group selected from the group consisting of methyl, ethyl, propyl, butyl, pentyl, hexyl, heptyl, octyl, and nonyl, or wherein $R_{12}$ is a cyclic hydrocarbyl group selected from the group consisting of cyclopropyl, cyclobutyl, cyclopentyl, cyclohexyl, cycloheptyl, cyclooctyl, and cyclononyl; and 1, 3, 5-tri-O-methylphloroglucinol;

(d) contacting the flavan-3-one provided by step (a) or obtained by step (b) with the compound containing having a nucleophilic aromatic moiety in the presence of a Lewis acid;

(e) forming an intermediate compound, wherein the compound having the nucleophilic aromatic moiety has a flavonoid base structure, the oxo group on the C-3 carbon of the flavan-3-one is converted to a hydroxy group and a I-3, II-6 or a I-3, II-8 C—C bond is formed by nucleophilic addition of the compound containing a nucleophilic aromatic moiety to the C-3 carbon of the flavan-3-one;

or forming an intermediate analogue compound, wherein the compound containing the nucleophilic aromatic moiety is 1, 3, 5-tri-methylphloroglucinol, the oxo group on the C-3 carbon of the flavan-3-one is converted to a hydroxy group and a I-3/1,3,5-tri-methylphloroglucinol C—C bond is formed by nucleophilic addition of the 1, 3, 5-tri-methylphloroglucinol to the C-3 carbon of the flavan-3-one;

(f) subjecting the intermediate compound or intermediate analogue compound to dehydration to introduce a double bond between the C-3 carbon and C-4 carbon contributed by the flavan-3-one portion to form a flavene compound substituted by the nucleophilic aromatic moiety on the C-3 carbon;

(g) optionally, subjecting the C-3 substituted flavene compound substituted by the nucleophilic aromatic moiety on the C-3 carbon of step (f) to hydroboration-oxidation hydration, thereby converting the double bond between the C-3 carbon and the C-4 carbon to a single bond and introducing a C-4 hydroxy group to form a C-4 hydroxy intermediate compound or C-4 hydroxy intermediate analogue compound;

(h) optionally, oxidizing the C-4 hydroxy intermediate compound or C-4 hydroxy intermediate analogue compound, wherein the C-4 hydroxy group converts to a C-4 oxo group, to form a biflavonoid, or a biflavonoid analogue which comprises 1,3,5-tri-methylphloroglucinol, which is substituted by the selected nucleophilic aromatic moiety on the C-3 carbon; wherein the C-3 coupled biflavonoid is formed from the nucleophilic aromatic moiety that has the flavonoid base structure and C-3 coupled biflavonoid analogue is formed from the nucleophilic aromatic moiety that is the 1,3,5-tri-O-methylphloroglucinol;

or alternatively to steps (g) and (h), (i) optionally subjecting the flavene compound substituted by the nucleophilic aromatic moiety on the C-3 carbon of step (f) to $OsO_4$ dihydroxylation, forming a dihydroxylated intermediate compound or a dihydroxylated intermediate analogue compound comprising a C-3 hydroxy group and a C-4 hydroxyl group and a single bond between the C-3 and C-4 carbons; and (j) optionally subjecting the dihydroxylated intermediate compound or dihydroxylated intermediate analogue compound to dehydration, introducing a double bond between the C-3 carbon and C-4 carbon to form an enol that rearranges to form the C-3 coupled biflavonoid or the C-3 coupled biflavonoid analogue having a C-4 oxo group and substituted by the nucleophilic aromatic moiety on the C-3 carbon, wherein the C-3 coupled biflavonoid is formed from the nucleophilic aromatic moiety that has the flavonoid base structure and C-3 coupled biflavonoid analogue is formed from the nucleophilic aromatic moiety that is the 1,3,5-tri-O-methylphloroglucinol.

2. The method according to claim 1, wherein the flavan-3-ol or the flavan-3-one is optically active.

3. The method according to claim 2, wherein the compound having a nucleophilic aromatic moiety has a flavonoid base structure, and wherein the C-3 coupled biflavonoid compound has the nucleophilic aromatic moiety on the C-3 carbon.

4. The method according to claim 2, wherein steps (g) and (h) or (i) and (j) are omitted and the biflavonoid or the biflavonoid analogue is an optically active C-3-C-4 flavene compound having an aromatic substituent on the C-3 carbon.

5. The method according to claim 1, wherein the compound having a nucleophilic aromatic moiety has a flavonoid base structure and wherein the biflavanoid compound is a I-3, II-6/8 coupled biflavonoid which is substituted by the nucleophilic aromatic moiety on the C-3 carbon.

6. The method according to claim 1, wherein the compound having a nucleophilic aromatic moiety is in the form of flavan-3-ol from 5,7,3',4'-tetrakis(methyloxy)flavan-3-one.

7. The method according to claim 1, wherein the compound having a nucleophilic aromatic moiety, the flavan-3-one, and the Lewis acid are mixed in an aprotic solvent.

8. A method for the preparation of a I-3,II-6/8 coupled poly-flavonoid or 1,3,5-tri-O-methylphloroglucinol-terminated poly-flavonoid analogue from a starting material or intermediate selected from the group consisting of flavan-3-ols and flavan-3-ones, the method comprising the steps of:

(a) providing a flavan-3-one of Formula (I) or a corresponding flavan-3-ol:

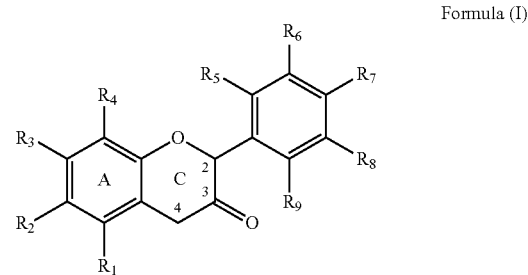

Formula (I)

wherein each of $R_1$, $R_2$, $R_3$, $R_4$, $R_5$, $R_6$, $R_7$, $R_8$ and $R_9$ is independently selected from the group consisting of hydrogen, —OH, a hydrocarbyl group; a saccharide moiety and —$OR_{10}$; wherein $R_{10}$ is selected from the group consisting of a hydrocarbyl group, an acyl group and a benzyl group; and wherein, the hydrocarbyl group in any one of $R_1$ to $R_{10}$ and/or the acyl group contains from 1 to 10 carbon atoms;

(b) optionally, converting the C-3 hydroxy group of the flavan-3-ol to an oxo group to form the flavan-3-one;

(c) providing a compound having a nucleophilic aromatic moiety, selected from the group consisting of a flavonoid base structure:

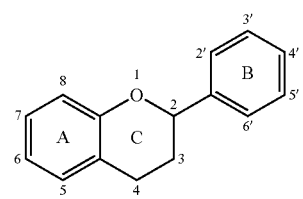

wherein carbon C-3 is substituted with —OH; and carbons C-2' to C-6' and C-5 to C-8 are unsubstituted or independently substituted with —OH, a saccharide moiety, $R_{11}$, $OR_{11}$ or $O—C(O)—R_{12}$, wherein $R_{11}$ is a linear hydrocarbyl group selected from the group consisting of methyl, ethyl, propyl, butyl, pentyl, hexyl, heptyl, octyl, nonyl, and decyl, or wherein $R_{11}$ is a cyclic hydrocarbyl group selected from the group consisting of cyclopropyl, cyclobutyl, cyclopentyl, cyclohexyl, cycloheptyl, cyclooctyl, cyclononyl, and cyclodecyl, or wherein $OR_{11}$ is O-benzyl;

wherein $R_{12}$ is a linear hydrocarbyl group selected from the group consisting of methyl, ethyl, propyl, butyl, pentyl, hexyl, heptyl, octyl, and nonyl, or wherein $R_{12}$ is a cyclic hydrocarbyl group selected from the group consisting of cyclopropyl, cyclobutyl, cyclopentyl, cyclohexyl, cycloheptyl, cyclooctyl, and cyclononyl;

(d) contacting the flavan-3-one provided by step (a) or obtained by step (b) with the compound having a nucleophilic aromatic moiety having a flavonoid base structure having a C-3 hydroxy group in the presence of a Lewis acid;

(e) forming a I-3, II-6/8 coupled compound where the 1-3 portion is coupled through the C-3 carbon of the flavan-3-one of step (d) or from the C-3 carbon of the nth oxo substituted coupled flavonoid of step (h) and where the II-6/8 portion is contributed by the nucleophilic aromatic moiety having a flavonoid base structure having a C-3 hydroxy group, wherein when coupling occurs the C-3 oxo group is converted to a hydroxy group and a C—C bond is formed between the I-3 portion and the II-6/8 portion;

(f) subjecting the I-3, II-6/8 coupled compound to dehydration, thereby introducing a double bond between the C-3 carbon and C-4 carbon of I-3 portion to form an intermediate compound while removing the C-3 hydroxy group and forming a flavene compound substituted on the C-3 carbon by the nucleophilic aromatic moiety;

(g) subjecting the flavene compound substituted by the nucleophilic aromatic moiety on the C-3 carbon of step (f) to hydroboration-oxidation hydration, thereby converting the double bond between the C-3 carbon and the C-4 carbon to a single bond and introducing a C-4 hydroxy group, to form a C-4 hydroxy intermediate compound;

(h) oxidizing the resulting intermediate compound, wherein the C-4 hydroxy group of the I-3 portion converts to a C-4 oxo group and the C-3 hydroxy group of the II-6/8 portion converts to an oxo group, forming an oxo group substituted coupled flavonoid that is a I-3, II-6/8 coupled poly-flavonoid;

(i) optionally, forming a poly-flavonoid by repeating n times the steps (d), (e), (f), (g), and (h), wherein n is 1 to 3, wherein the n compounds having a nucleophilic aromatic moiety having a flavonoid base structure with a hydroxy group at the C-3 position are the same or different;

(k) optionally, contacting the nth oxo group coupled poly-flavonoid with 1,3,5-tri-O-methylphloroglucinol in the presence of a Lewis acid;

(l) thereby forming a terminated coupled poly-flavonoid analogue intermediate compound, wherein the oxo group on the flavan-3-one is converted to a hydroxy group upon nucleophilic addition of the 1,3,5-tri-O-methylphloroglucinol;

(m) subjecting the terminated coupled poly-flavonoid analogue intermediate compound to dehydration to introduce a double bond between the C-3 carbon and C-4 carbon of the I-3 portion of the terminated coupled compound to form a terminated coupled poly-flavonoid analogue flavene intermediate compound;

(n) subjecting the terminated coupled poly-flavonoid analogue flavene intermediate compound to hydroboration-oxidation hydration, introducing a hydroxy group at the C-4 carbon of the I-3 portion to form a C-4 hydroxy terminal poly-flavonoid analogue intermediate compound;

(o) oxidizing the C-4 hydroxy terminated poly-flavonoid analogue intermediate compound to convert the hydroxy group at the C-4 carbon to an oxo group, forming a I-3, II-6/8 coupled 1,3,5-tri-O-methylphloroglucinol-terminated poly-flavonoid analogue;

or alternatively to steps (n) and (o), (p) subjecting the terminated coupled poly-flavonoid analogue flavene intermediate compound of step (m) to $OsO_4$ dihydroxylation, introducing a hydroxy group at the C-4 carbon and a hydroxy group at the C-3 carbon to form a dihydroxylated terminated poly-flavonoid analogue intermediate compound; and (q) subjecting the dihydroxylated terminated poly-flavonoid analogue intermediate compound to dehydration forming an enol product and allowing such enol product to rearrange spontaneously to form a 1-3, II-6/8 coupled 1,3,5-tri-O-methylphloroglucinol-terminated poly-flavonoid analogue.

\* \* \* \* \*